(12) United States Patent
Wang et al.

(10) Patent No.: US 12,054,503 B2
(45) Date of Patent: Aug. 6, 2024

(54) AMPHIPHILIC MATERIAL AND APPLICATION THEREOF IN PREPARATION FOR LIPOSOME

(71) Applicant: ZHEJIANG UNIVERSITY, Zhejiang (CN)

(72) Inventors: Guowei Wang, Zhejiang (CN); Pintong Huang, Zhejiang (CN); Yifan Jiang, Zhejiang (CN); Qunying Li, Zhejiang (CN); Chao Zhang, Zhejiang (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 9 days.

(21) Appl. No.: 18/021,613

(22) PCT Filed: Apr. 20, 2022

(86) PCT No.: PCT/CN2022/087887
§ 371 (c)(1),
(2) Date: Feb. 16, 2023

(87) PCT Pub. No.: WO2022/228230
PCT Pub. Date: Nov. 3, 2022

(65) Prior Publication Data
US 2023/0287020 A1    Sep. 14, 2023

(30) Foreign Application Priority Data
Apr. 26, 2021 (CN) .......................... 202110514793.9

(51) Int. Cl.
*C07F 9/09* (2006.01)
*A61K 9/127* (2006.01)
*A61K 31/7068* (2006.01)

(52) U.S. Cl.
CPC ............ *C07F 9/091* (2013.01); *A61K 9/1271* (2013.01); *A61K 31/7068* (2013.01)

(58) Field of Classification Search
None
See application file for complete search history.

(56) References Cited

U.S. PATENT DOCUMENTS

2009/0117079 A1*  5/2009  Monte ............... A61P 37/02
                                              424/93.1
2014/0004099 A1*  1/2014  Culp ................ A61P 7/06
                                              424/94.64
(Continued)

FOREIGN PATENT DOCUMENTS

CN    101444485 A    6/2009
CN    102740833 A    10/2012
(Continued)

OTHER PUBLICATIONS

Google Patents. English Translation of CN104193779A. https://patents.google.com/patent/CN104193779A/en?oq=CN+104193779 accessed on Jul. 10, 2023, originally published in Chinese on Dec. 10, 2014, pp. 1-9. (Year: 2014).*
(Continued)

*Primary Examiner* — Isaac Shomer
(74) *Attorney, Agent, or Firm* — Adam Warwisk Bell; Matthew Rupert Kaser

(57) ABSTRACT

The present invention relates to an amphiphilic material and an application thereof in preparation of a liposome, and in particular, the present invention provides an amphiphilic material, wherein the structure of the amphiphilic material is as follows. The amphiphilic material of the present invention is used for preparing drug-loaded nanoparticles to effectively enter cells such as tumor cells, thereby enhancing the therapeutic effect of the drug.

(Continued)

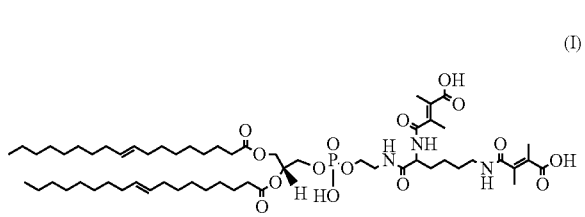

(I)

4 Claims, 7 Drawing Sheets

(56) References Cited

U.S. PATENT DOCUMENTS

| | | | | |
|---|---|---|---|---|
| 2016/0250177 | A1* | 9/2016 | McGhee | A61K 9/1271 424/450 |
| 2019/0091350 | A1* | 3/2019 | Peyman | A61K 49/227 |
| 2019/0351031 | A1* | 11/2019 | Wang | A61K 9/127 |

FOREIGN PATENT DOCUMENTS

| | | | |
|---|---|---|---|
| CN | 104193379 | A | 12/2014 |
| CN | 104193779 | A * | 12/2014 |
| CN | 104193779 | B * | 2/2016 |
| CN | 106999506 | A | 8/2017 |
| CN | 107115297 | A | 9/2017 |
| CN | 109998996 | A | 7/2019 |
| CN | 111481507 | A | 8/2020 |
| CN | 113307824 | A | 8/2021 |
| EP | 1439184 | A1 | 7/2004 |
| WO | WO0149268 | A1 | 7/2001 |
| WO | WO2008030807 | A2 | 3/2008 |

OTHER PUBLICATIONS

Yi-Ju Ho, Ju-Pi Li, Ching-Hsiang Fan, Hao-Li Liu, Chih-Kuang Yeh. "Ultrasound in tumor immunotherapy: Current status and future developments." Journal of Controlled Release 323 (2020) pp. 12-23. (Year: 2020).*

Balamurugan K and Chintamani P. "Lipid nano particulate drug delivery: An overview of the emerging trend." The Pharma Innovation Journal 2018; 7(7): 779-789. (Year: 2018).*

Ding, Jie et al. (Application of Liposome in Cancer Therapy and Tracer Study). Chinese Journal of Clinical Oncology. vol. 41. No. 21. Dec. 31, 2014. ISSN: 1000-8179, pp. 1403-1407.

* cited by examiner

US 12,054,503 B2

AMPHIPHILIC MATERIAL AND APPLICATION THEREOF IN PREPARATION FOR LIPOSOME

TECHNICAL FIELD

The present invention relates to the field of medicine. Specifically, the present invention relates to amphiphilic material and application thereof in preparation for liposome.

BACKGROUND TECHNOLOGY

Tumor is a serious life-threatening disease, and the research of anti-tumor drugs has become a research hotspot.

Although many anticancer drugs have been developed in the art, the anti-tumor effect is not ideal, the important reason is that anticancer drugs have poor tumor vascular permeability and are difficult to be absorbed by tumor cell, thus greatly limiting the therapeutic effect of anti-tumor drugs.

Tumor vascular endothelial cells are well organized and tightly stacked. Even when the drugs are delivered to the blood vessels of the tumor, it is difficult for the drugs to reach the microenvironment of the tumor site through the intercellular space of the vascular endothelial cells because the drugs are obstructed by the well-organized and tightly stacked vascular endothelial cells. Therefore, the existing anti-tumor drugs have low permeability in the tumor and cannot effectively accumulate in the tumor microenvironment, thus cannot exert anti-tumor effects. In addition, as for tumors, even though antitumor drugs penetrate into the tumor site from the intercellular space of the vascular endothelial cells, the antitumor drugs are mainly retained near the blood vessels after exuding from the tumor vessels, and rapidly return to the blood stream and are rapidly cleared in low-permeability tumors, which prevents the antitumor drugs from entering into the tumor cells, thus the antitumor drugs are unable to effectively exert antitumor effects.

Therefore, it is urgent to develop a drug with excellent therapeutic effect on tumors in the art.

SUMMARY OF THE INVENTION

It is an object of the present invention to provide an amphiphilic material, the amphiphilic material is used for preparing nanometer particle such as liposome that can effectively enter cells (e.g., tumor cells), thereby enhancing the therapeutic effect of the drug.

In the first aspect of the present invention, it provides an amphiphilic material, the structure of the amphiphilic material is as follows:

In the second aspect of the present invention, it provides a use of the amphiphilic material according to the first aspect of the present invention in the preparation of a nanometer particle.

Preferably, the particle size of the nanometer particle is 200-500 nm, preferably 300-450 nm, more preferably 330-400 nm, more preferably 360-400 nm, more preferably 370-390nm.

Preferably, the amphiphilic material promotes the nanometer particle into tumor cell.

Preferably, the amphiphilic material promotes the nanometer particle into tumor cell via endocytosis transport.

Preferably, the tumor comprises low permeability tumor.

Preferably, the tumor comprises solid tumor.

Preferably, the tumor comprises low permeability solid tumor.

Preferably, the tumor is selected from the group consisting of pancreatic cancer, glioma, and combinations thereof.

Preferably, the pancreatic cancer is pancreatic ductal adenocarcinoma.

Preferably, the pancreatic cancer is human pancreatic ductal adenocarcinoma.

Preferably, the glioma is cerebral glioma.

Preferably, the glioma is human cerebral glioma.

Preferably, the nanometer particle comprises the amphiphilic material according to the first aspect of the present invention.

Preferably, the nanometer particle is nanoparticle or liposome.

Preferably, the amphiphilic material is used as nanomaterial of the nanoparticle.

Preferably, the nanoparticle further comprises other nanomaterials.

Preferably, the nanomaterial comprises amphiphilic nanomaterial.

Preferably, the other nanomaterials are selected from the group consisting of polyethylene glycol-polylactic acid (PEG-PLA).

Preferably, the amphiphilic material is used as lipid material of the liposome.

Preferably, the liposome further comprises other lipid materials.

Preferably, the liposome material comprises amphiphilic lipid material.

Preferably, the other lipid materials are selected from the group consisting of 1,2-dipalmitoyl-sn-glycero-3-phosphocholine (DPPC), 1,2-distearoyl-sn-glycero-3-phosphoethanolamine-polyethylene glycol (DSPE-PEG), 1,2-dioleoyl-sn-glycero-3-phosphoethanolamine (DOPE), soy bean phospholipid, phosphatidylcholine (PC, lecithin), cholesterol, phosphatidylethanolamine (PE, cephalin), phosphati-

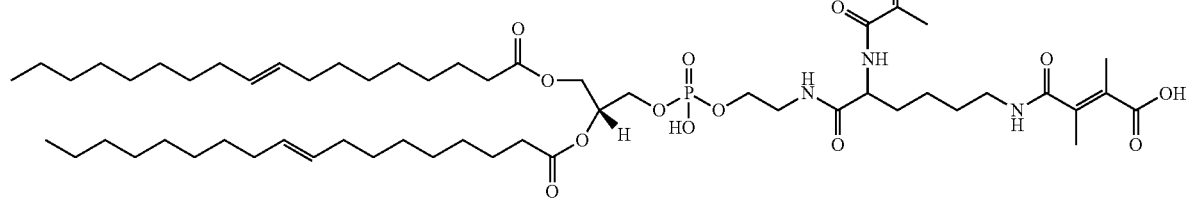

dylserine (PS), phosphatidylinositol (PI), phosphatidylglycerol (PG), dicetyl phosphate (DCP), dimyristoyl phosphatidylcholine (DMPC), distearoylphosphatidylcholine (DSPC), dilaurylphosphatidylcholine (DLPC), dioleoylphosphatidylcholine (DOPC), and combinations thereof.

Preferably, the lipid material comprises 1,2-dipalmitoyl-sn-glycero-3-phosphocholine (DPPC), the amphiphilic material according to the first aspect of the present invention and 1,2-distearoyl-sn-glycero-3-phosphoethanolamine-polyethylene glycol (DSPE-PEG).

Preferably, the 1,2-distearoyl-sn-glycero-3-phosphoethanolamine-polyethylene glycol (DSPE-PEG) is selected from the group consisting of DSPE-PEG600, DSPE-PEG800, DSPE-PEG1000, DSPE-PEG2000, DSPE-PEG4000, DSPE-PEG6000, and combinations thereof.

Preferably, the nanometer particle is drug-loaded nanometer particle.

Preferably, the amphiphilic material promotes the drug-loaded nanometer particle into tumor cell to enhance the killing effect of the drug on the tumor.

Preferably, the amphiphilic material promotes the drug-loaded nanometer particle into tumor cell via endocytosis transport to enhance the killing effect of the drug on the tumor.

Preferably, the drug comprises anticancer drug.

Preferably, the anticancer drug comprises chemical drug.

Preferably, the anticancer drug comprises gemcitabine, cytarabine, adriamycin, fluorouracil, and combinations thereof.

Preferably, the anticancer drug comprises gemcitabine.

Preferably, the drug comprises free drug or prodrug.

Preferably, the drug comprises prodrug.

Preferably, the prodrug comprises the prodrug obtained by modifying the free drug on the prodrug carrier.

Preferably, the modification comprises chemical modification and/or physical modification.

Preferably, the prodrug comprises the prodrug obtained by connecting the free drug with the prodrug carrier via chemical bonds.

Preferably, the drug is hydrophobic drug or hydrophilic drug.

Preferably, the free drug is hydrophobic drug or hydrophilic drug.

Preferably, the prodrug carrier is hydrophobic carrier or hydrophilic carrier.

Preferably, the prodrug carrier is higher fatty acid carrier or higher fatty alcohol carrier.

Preferably, the higher fatty acid carrier is selected from the group consisting of palmitic acid (hexadecanoic acid), margaric acid (heptadecanoic acid), stearic acid (octadecanoic acid), oleic acid (octadecenoic acid), linoleic acid (octadecadienoic acid), linolenic acid (octadecatrienoic acid), arachidic acid (eicosanoic acid), eicosapentaenoic acid, behenic acid (docosanoic acid), DHA (docosahexaenoic acid), lignoceric acid (tetracosanoic acid), and combinations thereof.

Preferably, the oleic acid comprises elaidic acid.

Preferably, the higher fatty alcohol carrier is selected from the group consisting of palmityl alcohol, stearyl alcohol, oleyl alcohol, linoleic alcohol, linolenic alcohol, arachidyl alcohol, eicosapentaenol, behenyl alcohol, docosahexaenol, and combinations thereof.

Preferably, the prodrug is amphiphilic prodrug.

Preferably, the amphiphilic prodrug is used as nanomaterial of the nanoparticle.

Preferably, the amphiphilic prodrug is used as lipid material of the liposome.

Preferably, the amphiphilic prodrug is used as lipid bilayer.

Preferably, the amphiphilic prodrug comprises a drug active ingredient as hydrophilic part and the prodrug carrier as hydrophobic part; or the amphiphilic prodrug comprises a drug active ingredient as hydrophobic part and the prodrug carrier as hydrophilic part.

Preferably, the prodrug comprises:

D-C wherein, "D" is drug active ingredient, "C" is prodrug carrier, and "-" is connection bond.

Preferably, the prodrug comprises:

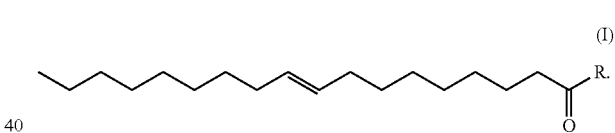

(I)

wherein. R is anticancer drug, the anticancer drug comprises gemcitabine, cytarabine, adriamycin, fluorouracil, and combinations thereof.

Preferably, the drug comprises gemcitabine elaidate.

Preferably, the prodrug comprises gemcitabine elaidate.

Preferably, the gemcitabine elaidate has the structure as follows:

CP4126

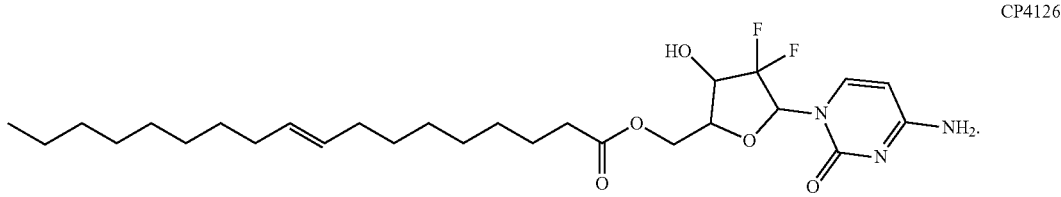

Preferably, the prodrug carrier is higher fatty acid containing 12-26 (preferably 14-22, more preferably 16-20) carbon atoms.

Preferably, the prodrug carrier is higher fatty alcohol containing 12-26 (preferably 14-22, more preferably 16-20) carbon atoms.

Preferably, the drug is loaded in the nanometer particle by one or more means selected from the group consisting of:

(i) the free drug is encapsulated into the nanometer particle; and/or (ii) the drug is used as nanomaterial or lipid material in the form of amphiphilic prodrug.

Preferably, the nanometer particle is prepared by film dispersion method, solvent evaporation method or ultrasonic method.

In the third aspect of the present invention, it provides a nanometer particle, the nanometer particle comprises the amphiphilic material according to the first aspect of the present invention.

Preferably, the particle size of the nanometer particle is 200-500 nm, preferably 300-450 nm, more preferably 330-400 nm, more preferably 360-400 nm, more preferably 370-390 nm.

Preferably, the nanometer particle is nanoparticle or liposome.

Preferably, the amphiphilic material is used as nanomaterial of the nanoparticle.

Preferably, the nanoparticle further comprises other nanomaterials.

Preferably, the nanomaterial comprises amphiphilic nanomaterial.

Preferably, the other nanomaterials are selected from the group consisting of polyethylene glycol-polylactic acid (PEG-PLA).

Preferably, the amphiphilic material is used as lipid material of the liposome.

Preferably, the liposome further comprises other lipid materials.

Preferably, the liposome material comprises amphiphilic lipid material.

Preferably, the other lipid materials are selected from the group consisting of 1,2-dipalmitoyl-sn-glycero-3-phosphocholine (DPPC), 1,2-distearoyl-sn-glycero-3-phosphoethanolamine-polyethylene glycol (DSPE-PEG), 1,2-dioleoyl-sn-glycero-3-phosphoethanolamine (DOPE), soy bean phospholipid, phosphatidylcholine (PC, lecithin), cholesterol, phosphatidylethanolamine (PE, cephalin), phosphatidylserine (PS), phosphatidylinositol (PI), phosphatidylglycerol (PG), dicetyl phosphate (DCP), dimyristoylphosphatidylcholine (DMPC), distearoylphosphatidylcholine (DSPC), dilaurylphosphatidylcholine (DLPC), dioleoylphosphatidylcholine (DOPC), and combinations thereof.

Preferably, the 1,2-distearoyl-sn-glycero-3-phosphoethanolamine-polyethylene glycol (DSPE-PEG) is selected from the group consisting of DSPE-PEG600, DSPE-PEG800, DSPE-PEG1000, DSPE-PEG2000, DSPE-PEG4000, DSPE-PEG6000, and combinations thereof.

Preferably, the lipid material comprises 1,2-dipalmitoyl-sn-glycero-3-phosphocholine (DPPC), the amphiphilic material according to the first aspect of the present invention and 1,2-distearoyl-sn-glycero-3-phosphoethanolamine-polyethylene glycol (DSPE-PEG).

Preferably, the nanometer particle is non drug-loaded or drug-loaded nanometer particle.

In the fourth aspect of the present invention, it provides a use of the nanometer particle according to the third aspect of the present invention for loading drug.

Preferably, the nanometer particle promotes the drug (e.g., anticancer drug) into tumor cell to enhance the killing effect of the drug on the tumor.

Preferably, the nanometer particle promotes the drug (e.g., anticancer drug) into tumor cell via endocytosis transport to enhance the killing effect of the drug on the tumor.

Preferably, the drug comprises anticancer drug.

Preferably, the anticancer drug comprises chemical drug.

Preferably, the anticancer drug comprises gemcitabine, cytarabine, adriamycin, fluorouracil, and combinations thereof.

Preferably, the anticancer drug comprises gemcitabine.

Preferably, the drug comprises free drug or prodrug.

Preferably, the drug comprises prodrug.

Preferably, the prodrug comprises the prodrug obtained by modifying the free drug on the prodrug carrier.

Preferably, the modification comprises chemical modification and/or physical modification.

Preferably, the prodrug comprises the prodrug obtained by connecting the free drug with the prodrug carrier via chemical bonds.

Preferably, the drug is hydrophobic drug or hydrophilic drug.

Preferably, the free drug is hydrophobic drug or hydrophilic drug.

Preferably, the prodrug carrier is hydrophobic carrier or hydrophilic carrier.

Preferably, the prodrug carrier is higher fatty acid carrier or higher fatty alcohol carrier.

Preferably, the prodrug carrier is higher fatty acid containing 12-26 (preferably 14-22, more preferably 16-20) carbon atoms.

Preferably, the prodrug carrier is higher fatty alcohol containing 12-26 (preferably 14-22, more preferably 16-20) carbon atoms.

Preferably, the higher fatty acid carrier is palmitic acid (hexadecanoic acid), margaric acid (heptadecanoic acid), stearic acid (octadecanoic acid), oleic acid (octadecenoic acid), linoleic acid (octadecadienoic acid), linolenic acid (octadecatrienoic acid), arachidic acid (eicosanoic acid), eicosapentaenoic acid, behenic acid (docosanoic acid), DHA (docosahexaenoic acid) or lignoceric acid (tetracosanoic acid).

Preferably, the oleic acid comprises elaidic acid.

Preferably, the higher fatty alcohol carrier is selected from the group consisting of palmityl alcohol, stearyl alcohol, oleyl alcohol, linoleic alcohol, linolenic alcohol, arachidyl alcohol, eicosapentaenol, behenyl alcohol, docosahexaenol, and combinations thereof.

Preferably, the prodrug is amphiphilic prodrug.

Preferably, the amphiphilic prodrug is used as nanomaterial of the nanoparticle.

Preferably, the amphiphilic prodrug is used as lipid material of the liposome.

Preferably, the amphiphilic prodrug is used as lipid bilayer.

Preferably, the amphiphilic prodrug comprises a drug active ingredient as hydrophilic part and the prodrug carrier as hydrophobic part; or the amphiphilic prodrug comprises a drug active ingredient as hydrophobic part and the prodrug carrier as hydrophilic part.

Preferably, the prodrug comprises.

D-C wherein, "D" is drug active ingredient, "C" is prodrug carrier, and "-" is connection bond.

Preferably, the prodrug comprises:

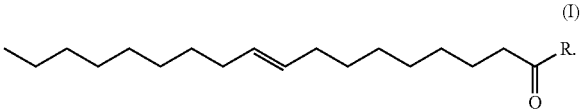

(I)

wherein, R is anticancer drug, the anticancer drug comprises gemcitabine, cytarabine, adriamycin, fluorouracil, and combinations thereof.

Preferably, the drug comprises gemcitabine elaidate.

Preferably, the prodrug comprises gemcitabine elaidate.

Preferably, the gemcitabine elaidate has the structure as follows:

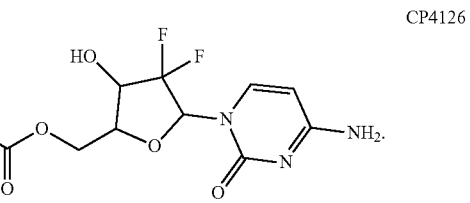

CP4126

Preferably, the drug is loaded in the nanometer particle by one or more means selected from the group consisting of:
(i) the free drug is encapsulated into the nanometer particle; and/or
(ii) the drug is used as nanomaterial or lipid material in the form of amphiphilic prodrug.

In the fifth aspect of the present invention, it provides a liposome, the liposome comprises lipid material and prodrug;

the lipid material comprises 1,2-dipalmitoyl-sn-glycero-3-phosphocholine (DPPC), the amphiphilic material according to the first aspect of the present invention and 1,2-distearoyl-sn-glycero-3-phosphoethanolamine-polyethylene glycol (DSPE-PEG).

Preferably, the particle size of the liposome is 200-500 nm, preferably 300-450 nm, more preferably 330-400 nm, more preferably 360-400 nm, more preferably 370-390 nm.

Preferably, the lipid material is used as lipid bilayer.

Preferably, the prodrug is used as lipid material of the liposome.

Preferably, the prodrug is used as lipid bilayer.

Preferably, the 1,2-distearoyl-sn-glycero-3-phosphoethanolamine-polyethylene glycol (DSPE-PEG) is selected from the group consisting of DSPE-PEG600, DSPE-PEG800, DSPE-PEG1000, DSPE-PEG2000, DSPE-PEG4000, DSPE-PEG6000, and combinations thereof.

Preferably, the prodrug comprises the prodrug obtained by modifying the free drug on the prodrug carrier.

Preferably, the free drug comprises anticancer drug.

Preferably, the anticancer drug comprises chemical drug.

Preferably, the anticancer drug comprises gemcitabine, cytarabine, adriamycin, fluorouracil, and combinations thereof.

Preferably, the anticancer drug comprises gemcitabine.

Preferably, the modification comprises chemical modification and/or physical modification.

Preferably, the prodrug comprises the prodrug obtained by connecting the free drug with the prodrug carrier via chemical bonds.

Preferably, the free drug is hydrophobic drug or hydrophilic drug.

Preferably, the prodrug carrier is hydrophobic carrier or hydrophilic carrier.

Preferably, the prodrug carrier is higher fatty acid carrier or higher fatty alcohol carrier.

Preferably, the prodrug carrier is higher fatty acid containing 12-26 (preferably 14-22, more preferably 16-20) carbon atoms.

Preferably, the prodrug carrier is higher fatty alcohol containing 12-26 (preferably 14-22, more preferably 16-20) carbon atoms.

Preferably, the higher fatty acid carrier is selected from the group consisting of palmitic acid (hexadecanoic acid), margaric acid (heptadecanoic acid), stearic acid (octadecanoic acid), oleic acid (octadecenoic acid), linoleic acid (octadecadienoic acid), linolenic acid (octadecatrienoic acid), arachidic acid (eicosanoic acid), eicosapentaenoic acid, behenic acid (docosanoic acid), DHA (docosahexaenoic acid), lignoceric acid (tetracosanoic acid), and combinations thereof.

Preferably, the higher fatty alcohol carrier is selected from the group consisting of palmityl alcohol, stearyl alcohol, oleyl alcohol, linoleic alcohol, linolenic alcohol, arachidyl alcohol, eicosapentaenol, behenyl alcohol, docosahexaenol, and combinations thereof.

Preferably, the oleic acid comprises elaidic acid.

Preferably, the prodrug is amphiphilic prodrug.

Preferably, the amphiphilic prodrug comprises a drug active ingredient as hydrophilic part and the prodrug carrier as hydrophobic part; or the amphiphilic prodrug comprises a drug active ingredient as hydrophobic part and the prodrug carrier as hydrophilic part.

Preferably, the prodrug comprises.

D-C wherein, "D" is drug active ingredient, "C" is prodrug carrier, and "-" is connection bond.

Preferably, the prodrug comprises:

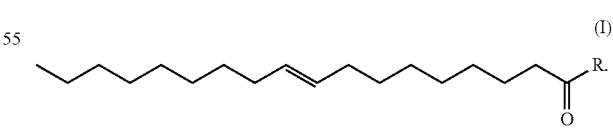

(I)

wherein, R is anticancer drug, the anticancer drug comprises gemcitabine, cytarabine, adriamycin, fluorouracil, and combinations thereof.

Preferably, the drug comprises gemcitabine elaidate.

Preferably, the prodrug comprises gemcitabine elaidate.

Preferably, the gemcitabine elaidate has the structure as follows:

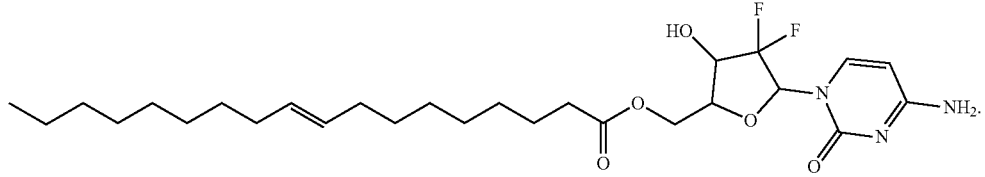

CP4126

Preferably, the liposome further comprises water, buffer solution and/or perfluoropentane.

Preferably, the lipid bilayer encapsulates water, buffer solution and/or perfluoropentane.

Preferably, the liposome encapsulates water, buffer solution and/or perfluoropentane.

Preferably, the buffer solution comprises glycerol-contained phosphate buffer saline.

Preferably, the volume fraction of the glycerol is 5-15%, preferably 8-12%, more preferably 10% in the glycerol-contained phosphate buffer saline.

Preferably, the concentration of the glycerol-contained phosphate buffer saline is 5-15 mM, preferably 8-12 mM, more preferably 10 mM, based on the concentration of phosphate radical.

Preferably, the pH of the glycerol-contained phosphate buffer saline is 7.2-7.6, preferably 7.4.

Preferably, the lipid bilayer encapsulates perfluoropentane and/or glycerol-contained phosphate buffer saline.

Preferably, the weight ratio of the 1,2-dipalmitoyl-sn-glycero-3-phosphocholine (DPPC) to the amphiphilic material according to the first aspect of the present invention is 0.2-2:0.2-2, preferably 0.5-1.5:0.5-1.5, more preferably 0.8-1.2:0.8-1.2, most preferably 1:1.

Preferably, the molar ratio of the 1,2-dipalmitoyl-sn-glycero-3-phosphocholine (DPPC) to the amphiphilic material according to the first aspect of the present invention is 0.5-3:1, preferably 1-2:1, more preferably 1.3-1.7:1.

Preferably, the weight ratio of the 1,2-dipalmitoyl-sn-glycero-3-phosphocholine (DPPC) to the 1,2-distearoyl-sn-glycero-3-phosphoethanolamine-polyethylene glycol (DSPE-PEG) is 0.5-5:1, preferably 0.8-3:1, more preferably 1-2:1, more preferably 1.3-1.7:1, most preferably 1.5:1.

Preferably, the molar ratio of the 1,2-dipalmitoyl-sn-glycero-3-phosphocholine (DPPC) to the 1,2-distearoyl-sn-glycero-3-phosphoethanolamine-polyethylene glycol (DSPE-PEG) is 3-10:1, preferably 5-7:1, more preferably 5-6.5:1, more preferably 5.5-6.3:1, most preferably 5.6-6.0:1.

Preferably, the weight ratio of the amphiphilic material according to the first aspect of the present invention to the 1,2-distearoyl-sn-glycero-3-phosphoethanolamine-polyethylene glycol (DSPE-PEG) is 0.5-5:1, preferably 0.8-3:1, more preferably 1-2:1, more preferably 1.3-1.7:1, most preferably 1.5:1.

Preferably, the molar ratio of the amphiphilic material according to the first aspect of the present invention to the 1,2-distearoyl-sn-glycero-3-phosphoethanolamine-polyethylene glycol (DSPE-PEG) is 3-7:1, preferably 4-6:1, more preferably 3-5:1, more preferably 3.3-4.5:1, most preferably 3.6-4.0:1.

Preferably, the weight ratio of the 1,2-dipalmitoyl-sn-glycero-3-phosphocholine (DPPC) to the prodrug is 0.5-5:1, preferably 0.8-3:1, more preferably 1-2:1, more preferably 1.3-1.7:1, most preferably 1.5:1.

Preferably, the molar ratio of the 1,2-dipalmitoyl-sn-glycero-3-phosphocholine (DPPC) to the prodrug is 0.5-3:1, preferably 0.5-1.5:1, more preferably 0.8-1.5:1, more preferably 0.9-1.3:1, most preferably 1.0-1.2:1.

Preferably, the weight ratio of the amphiphilic material according to the first aspect of the present invention to the prodrug is 0.5-5:1, preferably 0.8-3:1, more preferably 1-2:1, more preferably 1.3-1.7:1, most preferably 1.5:1.

Preferably, the molar ratio of the amphiphilic material according to the first aspect of the present invention to the prodrug is 0.5-1.5:1, more preferably, 0.5-1.0:1, and 0.6-0.9:1.

Preferably, the weight ratio of the 1,2-distearoyl-sn-glycero-3-phosphoethanolamine-polyethylene glycol (DSPE-PEG) to the prodrug is 0.2-2:0.2-2, preferably 0.5-1.5:0.5-1.5, more preferably 0.8-1.2:0.8-1.2, most preferably 1:1.

Preferably, the molar ratio of the 1,2-distearoyl-sn-glycero-3-phosphoethanolamine-polyethylene glycol (DSPE-PEG) to the prodrug is 1:2-8, more preferably 1:3-7, most preferably 1:4.5-6.5.

Preferably, the mass volume ratio (mg:μl) of the 1,2-dipalmitoyl-sn-glycero-3-phosphocholine (DPPC) to the perfluoropentane is 1:20-50, preferably 1:20-40, more preferably 1:25-38, more preferably 1:30-35, more preferably 1:22-34.

Preferably, the mass volume ratio (mg:μl) of the amphiphilic material according to the first aspect of the present invention to the perfluoropentane is 1:20-50, more preferably 1:20-40, more preferably 1:25-38, more preferably 1:30-35, most preferably 1:32-34.

Preferably, the mass volume ratio (mg:μl) of the 1,2-distearoyl-sn-glycero-3-phosphoethanolamine-polyethylene glycol (DSPE-PEG) to the perfluoropentane is 1:30-70, preferably 1:40-60, more preferably 1:45-55, more preferably 1:48-52.

Preferably, the volume ratio of the perfluoropentane to the buffer solution is 1:40-80, preferably 1:50-70, more preferably 1:55-65, more preferably 1:58-62.

Preferably, the volume ratio of the perfluoropentane to the glycerol-contained phosphate buffer saline is 1:40-80, preferably 1:50-70, more preferably 1:55-65, more preferably 1:58-62.

In the sixth aspect of the present invention, it provides a method for preparing the liposome according to the fifth aspect of the present invention, which comprises the following steps:

(1) dissolving the lipid material and the prodrug in an organic solvent, and removing the organic solvent to obtain a lipid film;

(2) hydrating the lipid film with perfluoropentane and buffer solution, and stirring to obtain the liposome.

Preferably, in the step (1), the organic solvent is selected from the group consisting of chloroform, dichloromethane, and combinations thereof.

Preferably, in the step (1), the weight volume ratio (mg: ml) of the lipid material to the organic solvent is preferably 1-5:1, more preferably 1-3:1, more preferably 1.5-2.5:1, more preferably 1.8-2.2:1.

Preferably, in the step (1), the weight volume ratio (mg: ml) of the prodrug to the organic solvent is 0.2-2:1, preferably 0.2-1.5:1, more preferably 0.2-0.8:1, more preferably 0.4-0.6:1.

Preferably, the weight volume ratio (mg: ml) of the 1,2-dipalmitoyl-sn-glycero-3-phosphocholine (DPPC) to the organic solvent is 0.3-5:1, preferably 0.3-3:1, more preferably 0.3-2:1, more preferably 0.5-1:1, more preferably 0.6-0.8:1.

Preferably, the volume ratio of the perfluoropentane to the glycerol-contained phosphate buffer saline is 1:40-80, preferably 1:50-70, more preferably 1:55-65, more preferably 1:58-62.

Preferably, in the step (1), the organic solvent is removed by rotary evaporation under reduced pressure.

Preferably, in the step (1), the organic solvent is removed by rotary evaporation under reduced pressure at 35-40° C.

Preferably, in the step (2), the perfluoropentane and the buffer solution are added sequentially to the lipid film to hydrate the lipid film.

Preferably, in the step (2), the hydration is carried out at a low temperature.

Preferably, the low temperature is 2-10° C., preferably 2-6° C.

Preferably, in the step (2), the stirring comprises the following steps:

stiring at low temperature firstly, and then stiring at rising temperature.

Preferably, the low temperature is 2-10° C., preferably 2-6° C.

Preferably, the stirring time under the low temperature is 0.5-1.5 h, preferably 0.8-1.2 h, more preferably 1 h.

Preferably, the rising temperature is 20-40° C., preferably 25-35° C., more preferably 28-32° C.

Preferably, the stirring time under the rising temperature is 0.5-1.5 h, preferably 0.8-1.2 h, more preferably 1 h.

Preferably, the stirring comprises magnetic stirrer stirring.

Preferably, in the stirring at rising temperature, the container in which the stirring solution is placed is open.

Preferably, the stirring at rising temperature can remove the unencapsulated perfluoropentane.

Preferably, the liposome is in the form of liposome nanodroplet.

Preferably, the encapsulated rate of the liposome is ≥90%, preferably ≥95%, more preferably ≥99%, most preferably 100%.

Preferably, the drug loading rate of the liposome is 8-15 wt %, preferably 9-11 wt %.

Preferably, the method comprises the following steps:
(i) dissolving the DPPC, the amphiphilic material according to the first aspect of the present invention, DSPE-PEG and gemcitabine elaidate in chloroform, and removing the solvent by rotary evaporation under reduced pressure to obtain the lipid film in round bottom flask;
(ii) cooling the lipid film to 2-6° C., and adding perfluoropentane to immerse the lipid film, then adding glycerol-contained phosphate buffer saline to hydrate, stirring for 0.8-1.2 h at 2-6° C., and then stirring for 0.8-1.2 h at 25-35° C. in the open round bottom flask to obtain the liposome.

Preferably, the method comprises the following steps:
(i) dissolving 1.2-1.8 mg of DPPC, 1.2-1.8 mg of the amphiphilic material according to the first aspect of the present invention, 0.8-1.2 mg of DSPE-PEG and 0.8-1.2 mg of gemcitabine elaidate in chloroform, and removing the solvent by rotary evaporation under reduced pressure to obtain the lipid film in round bottom flask;
(ii) cooling the lipid film to 2-6° C., and adding 45-55 µL of perfluoropentane to immerse the lipid film, then adding 2.8-3.2 mL of glycerol-contained phosphate buffer saline to hydrate, stirring for 0.8-1.2 h at 2-6° C., and then stirring for 0.8-1.2 h at 25-35° C. in the open round bottom flask to obtain the liposome.

In the seventh aspect of the present invention, it provides a composition, the composition comprises the nanometer particle according to the third aspect of the present invention and/or the liposome according to the fifth aspect of the present invention.

Preferably, the composition is a pharmaceutical composition.

Preferably, the pharmaceutical composition further comprises a pharmaceutically acceptable carrier.

Preferably, the composition is solid preparation, liquid preparation or semi-solid preparation.

Preferably, the composition is injection preparation, oral preparation or external preparation.

Preferably, the injection preparation is intravenous injection preparation, intratumoral injection preparation, tumor intravascular injection preparation or tumor microenvironment injection preparation.

In the eighth aspect of the present invention, it provides a use of the nanometer particle according to the third aspect of the present invention and/or the liposome according to the fifth aspect of the present invention in the preparation of a composition for the prevention and/or treatment of disease.

Preferably, the nanometer particle is drug-loaded nanometer particle.

Preferably, the disease is an indication disease of the drug

Preferably, the disease comprises tumor.

Preferably, the composition is a pharmaceutical composition.

Preferably, the pharmaceutical composition further comprises a pharmaceutically acceptable carrier.

Preferably, the composition is solid preparation, liquid preparation or semi-solid preparation.

Preferably, the composition is injection preparation, oral preparation or external preparation.

Preferably, the injection preparation is intravenous injection preparation, intratumoral injection preparation, tumor intravascular injection preparation or tumor microenvironment injection preparation.

Preferably, the prodrug comprises the prodrug of anticancer drug, and the disease comprises tumor.

Preferably, the tumor comprises low permeability tumor.

Preferably, the tumor comprises solid tumor.

Preferably, the tumor comprises low permeability solid tumor.

Preferably, the tumor is selected from the group consisting of pancreatic cancer, glioma, and combinations thereof.

Preferably, the pancreatic cancer is pancreatic ductal adenocarcinoma.

Preferably, the pancreatic cancer is human pancreatic ductal adenocarcinoma.

Preferably, the glioma is cerebral glioma.

Preferably, the glioma is human cerebral glioma.

Preferably, the treatment comprises inhibition, alleviation, relief, reversal or eradication.

In the ninth aspect of the present invention, it provides a system or device for treating disease, the system comprises the nanometer particle according to the third aspect of the present invention and/or the liposome according to the fifth aspect of the present invention; and an ultrasound device.

Preferably, the system or device further comprises a label, the specification or label records that an ultrasound stimulation is carried out on the lesion site (e.g., tumor site) during the administration of the nanometer particle according to the third aspect of the present invention and/or the liposome according to the fifth aspect of the present invention to a subject in need for the prevention and/or treatment of disease.

Preferably, the nanometer particle is drug-loaded nanometer particle.

Preferably, the ultrasound device comprises ultrasonic instrument.

Preferably, the subject comprises human and non-human mammal.

Preferably, the non-human mammal comprises cattle, horse, sheep, dog, cat or mouse.

Preferably, the disease is an indication disease of the drug

Preferably, the disease comprises tumor.

Preferably, the prodrug comprises the prodrug of anticancer drug, and the disease comprises tumor.

Preferably, the tumor comprises low permeability tumor.

Preferably, the tumor comprises solid tumor.

Preferably, the tumor comprises low permeability solid tumor.

Preferably, the tumor is selected from the group consisting of pancreatic cancer, glioma, and combinations thereof.

Preferably, the pancreatic cancer is pancreatic ductal adenocarcinoma.

Preferably, the pancreatic cancer is human pancreatic ductal adenocarcinoma.

Preferably, the glioma is cerebral glioma.

Preferably, the glioma is human cerebral glioma.

Preferably, the administration is injection administration, oral administration or external administration.

Preferably, the injection administration is intravenous injection administration, intratumoral injection administration, tumor intravascular injection administration or tumor microenvironment injection administration.

In the tenth aspect of the present invention, it provides a method for preventing and/or treating disease, which comprises administering the nanometer particle according to the third aspect of the present invention and/or the liposome according to the fifth aspect of the present invention to a subject in need, thereby treating disease.

Preferably, the nanometer particle is drug-loaded nanometer particle.

Preferably, the subject comprises human and non-human mammal.

Preferably, the non-human mammal comprises cattle, horse, sheep, dog, cat or mouse.

Preferably, the disease is an indication disease of the drug

Preferably, the disease comprises tumor.

Preferably, the prodrug comprises the prodrug of anticancer drug, and the disease comprises tumor.

Preferably, the tumor comprises low permeability tumor.

Preferably, the tumor comprises solid tumor.

Preferably, the tumor comprises low permeability solid tumor.

Preferably, the tumor is selected from the group consisting of pancreatic cancer, glioma, and combinations thereof.

Preferably, the pancreatic cancer is pancreatic ductal adenocarcinoma.

Preferably, the pancreatic cancer is human pancreatic ductal adenocarcinoma.

Preferably, the glioma is cerebral glioma.

Preferably, the glioma is human cerebral glioma.

Preferably, an ultrasound stimulation is carried out on the lesion site (e.g., tumor site) during the administration of the nanometer particle according to the third aspect of the present invention and/or the liposome according to the fifth aspect of the present invention to a subject in need.

Preferably, the administration is injection administration, oral administration or external administration.

Preferably, the injection administration is intravenous injection administration, intratumoral injection administration, tumor intravascular injection administration or tumor microenvironment injection administration.

It should be understood that, in the present invention, each of the technical features specifically described above and below (such as those in the Examples) can be combined with each other, thereby constituting new or preferred technical solutions.

EMBODIMENTS FOR CARRYING OUT THE INVENTION

Figure 1:
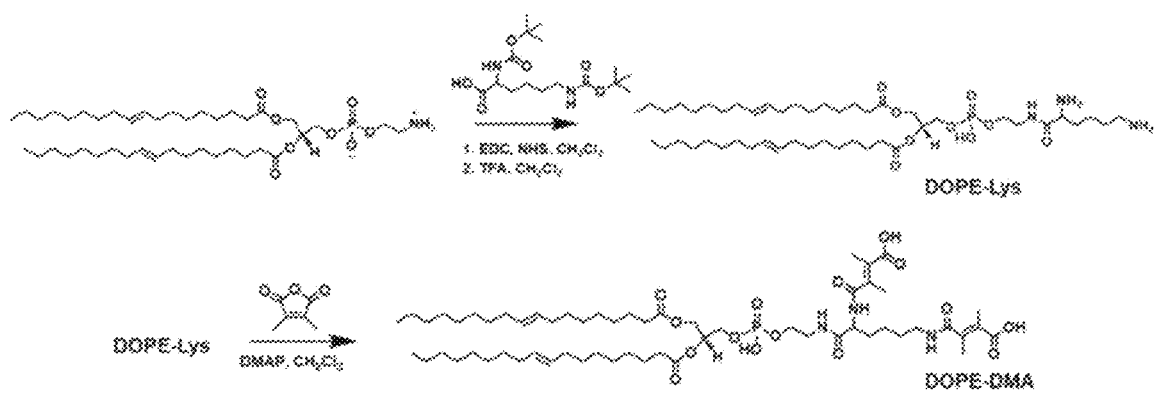
FIG. 1 shows the synthetic route of DOPE-DMA.

The present invention develops an amphiphilic material with novel structure. The drug-loaded nanometer particle (e.g., drug-loaded liposome) prepared by the amphiphilic material can effectively enter cells ((e.g., tumor cell), thereby enhancing the therapeutic effect of drug. Specifically, the experiment results of the present invention show that the amphiphilic material of the present invention, as the lipid material of drug-loaded liposome, can significantly promote the drug-loaded liposome into tumor cells and enhance the anti-tumor effect of the drug. The experiment results of the present invention further show that the drug-loaded liposome prepared by the amphiphilic material of the present invention has excellent long blood clearance half-life, can significantly expand or increase the openings in the vascular endothelial cells under ultrasound stimulation, promote the drug-loaded liposome to penetrate the tumor site from the blood vessels, significantly promote the drug-loaded liposome into the tumor cells, and avoid the retention and degradation of lysosome, thereby enhancing the anti-tumor effect of drug.

Terms

Unless otherwise defined, all technical and scientific terms used herein have the same meaning as commonly understood by the skilled in the art of the invention.

As used herein, the term "comprise", "comprising", and "containing" are used interchangeably, which not only comprise closed definitions, but also semi-closed and open definitions. In other words, the term comprises "consisting of" and "essentially consisting of".

As used herein, the relevant terms are shown in Table A below.

TABLE A

| | cryo-transmission electron | Cryo-transmission electron |
|---|---|---|
| cryo-TEM | microscope | microscope |
| DOPE | 1,2-Dioleoyl-sn-glycero-3-phosphoethanolamine(CAS No. 4004-05-1) | 1,2-Dioleoyl-sn-glycero-3-phosphoethanolamine |
| DOPE-DMA | dimethylmaleic anhydride-modified DOPE | Dimethylmaleic anhydride-modified 1,2-Dioleoyl-sn-glycero-3-phosphoethanolamine-lysine |
| DOPE-SA | succinic anhydride-modified DOPE | Succinic anhydride-modified 1,2-Dioleoyl-sn-glycero-3-phosphoethanolamine-lysine |
| DSPE-PEG2000 | 1,2-distearyl-sn-glycerol-3-phosphoethanolamine-polyethylene glycol 2000 (CAS No. 147867-65-0) | 1,2-distearyl-sn-glycero-3-phosphoethanolamine-polyethylene glycol 2000, also known as distearoyl phosphoethanolamine-polyethylene glycol 2000 |
| DPPC | 1,2-dipalmitoyl-sn-glycero-3-phosphocholine (CAS No. 2797-68-4) | 1,2-dipalmitoyl-sn-glycero-3-phosphocholine, also known as dipalmitoyl phosphatidylcholine |
| FBS | fetal bovine serum | Fetal bovine serum |
| GEM | gemcitabine | Free gemcitabine |
| Cy5 | Fluorescent resonance energy transfer (FRET) dye Cy5 (λex/em: 640/670 nm) | |
| TUNEL | TdT-mediated dUTP nick end labeling | TdT-mediated dUTP nick end labeling |
| $^1$H-NMR | proton nuclear magnetic resonance | Proton nuclear magnetic resonance |
| MALDI-TOF-MS | matrix-assisted laser desorption ionization time-of-flight mass spectrometry | matrix-assisted laser desorption ionization time-of-flight mass spectrometry |
| CLSM | Laser scanning confocal microscope | |

As used herein, the term "IC$_{50}$" refers to 50% inhibiting concentration, ie, the concentration of the inhibitor when 50% inhibition effect is achieved.

As used herein, the terms "gemcitabine prodrug CP4126" and "CP4126" are used interchangeably, and the structure of gemcitabine prodrug CP4126 is as follows.

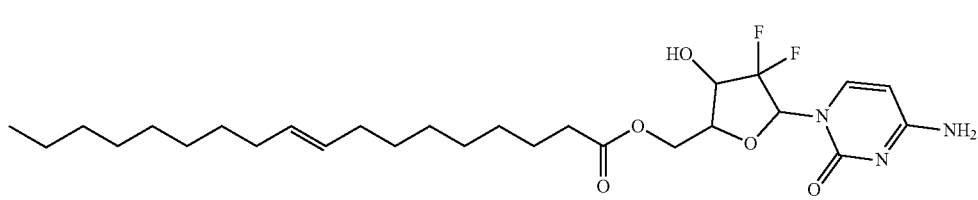

CP4126

As used herein, the term "glycerol-contained phosphate buffer saline" refers to a phosphate buffer saline solution containing glycerol, wherein the concentration (e.g., mM) refers to the concentration of phosphate radical.

In the present invention, the term "prevention" refers to a method of preventing the occurrence of disease and/or its complications, or protecting a subject from getting disease.

In the present invention, the term "treatment" comprises inhibiting, alleviating, relieving, reversing or eradication the progression of the disease, and does not require 100% inhibition, elimination and reversal. In some embodiments, compared to the level observed in the absence of the drug-loaded nanometer particle and the liposome of the present invention, the drug-loaded nanometer particle and the liposome of the present invention alleviates, inhibits and/or reverses related diseases (e.g., tumor) and its complications such as at least about 10%, at least about 30%, at least about 50%, at least about 80%, at least about 90%, at least about 95%, or at least about 100%.

In the present invention, the term "tumor" and "cancer" are used interchangeably.

Amphiphilic Material and Use Thereof

The present invention provides an amphiphilic material. Preferably, the structure of the amphiphilic material is as follows.

Preferably, the amphiphilic material promotes the drug-loaded nanometer particle into tumor cell via endocytosis transport to enhance the killing effect of the drug on the tumor.

Preferably, the nanometer particle is prepared by film dispersion method, solvent evaporation method or ultrasonic method.

Drug

The drug of the present invention can be loaded in the nanometer particle to exert therapeutic effect on the disease The drug of the present invention is not particularly limited. Preferably, the drug comprises anticancer drug.

Preferably, the anticancer drug comprises chemical drug, for example, the anticancer drug comprises gemcitabine, cytarabine, adriamycin, fluorouracil, and combinations thereof.

In a preferred embodiment, the drug comprises free drug or prodrug.

In a preferred embodiment, the drug comprises prodrug. The prodrug refers to the compound that can be obtained by chemical structure modification or physical modification of drug, and can release active drug in vivo via enzymatic or non-enzymatic transformation to exert drug effect.

In a preferred embodiment, the prodrug comprises the prodrug obtained by modifying the free drug on the prodrug carrier.

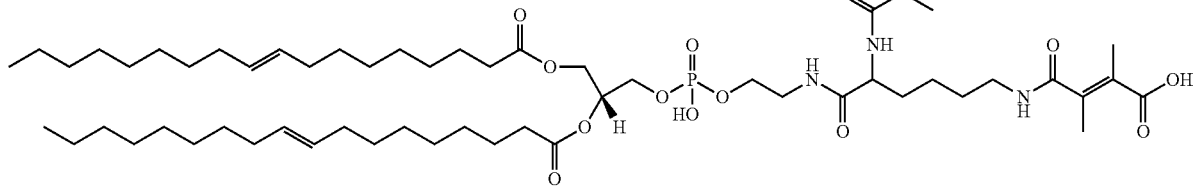

The present invention further provides a use of the amphiphilic material of the present invention in the preparation of a nanometer particle.

In a preferred embodiment, the amphiphilic material promotes the nanometer particle into tumor cell.

Preferably, the amphiphilic material promotes the nanometer particle into tumor cell via endocytosis transport.

In another preferred embodiment, the nanometer particle is drug-loaded nanometer particle.

Preferably, the amphiphilic material promotes the drug-loaded nanometer particle into tumor cell to enhance the killing effect of the drug on the tumor.

Preferably, the modification comprises chemical modification and/or physical modification. For example, the prodrug comprises the prodrug obtained by connecting the free drug with the prodrug carrier via chemical bonds.

In a preferred embodiment, the drug is hydrophobic drug or hydrophilic drug.

In a preferred embodiment, the free drug is hydrophobic drug or hydrophilic drug.

In a preferred embodiment, the prodrug carrier is hydrophobic carrier or hydrophilic carrier.

In a preferred embodiment, the prodrug carrier is higher fatty acid carrier or higher fatty alcohol carrier.

In a preferred embodiment, the prodrug carrier is higher fatty acid containing 12-26 (preferably 14-22, more preferably 16-20) carbon atoms.

In a preferred embodiment, the prodrug carrier is higher fatty alcohol containing 12-26 (preferably 14-22, more preferably 16-20) carbon atoms.

Representatively, the higher fatty acid carrier is selected from the group consisting of palmitic acid (hexadecanoic acid), margaric acid (heptadecanoic acid), stearic acid (octadecanoic acid), oleic acid (octadecenoic acid), linoleic acid (octadecadienoic acid), linolenic acid (octadecatrienoic acid), arachidic acid (eicosanoic acid), eicosapentaenoic acid, behenic acid (docosanoic acid), DHA (docosahexaenoic acid) or lignoceric acid (tetracosanoic acid), and combinations therefore.

In a preferred embodiment, the oleic acid comprises elaidic acid.

Representatively, the higher fatty alcohol carrier is selected from the group consisting of palmityl alcohol, stearyl alcohol, oleyl alcohol, linoleic alcohol, linolenic alcohol, arachidyl alcohol, eicosapentaenol, behenyl alcohol, docosahexaenol, and combinations thereof.

In a preferred embodiment, the prodrug is amphiphilic prodrug.

In a preferred embodiment, the amphiphilic prodrug is used as nanomaterial of the nanoparticle.

In a preferred embodiment, the amphiphilic prodrug is used as lipid material of the liposome.

Preferably, the amphiphilic prodrug is used as lipid bilayer.

In a preferred embodiment, the amphiphilic prodrug comprises a drug active ingredient as hydrophilic part and the prodrug carrier as hydrophobic part.

In a preferred embodiment, the amphiphilic prodrug comprises a drug active ingredient as hydrophobic part and the prodrug carrier as hydrophilic part.

In a preferred embodiment, the prodrug comprises:

D-C wherein, "D" is drug active ingredient, "C" is prodrug carrier, and "-" is connection bond.

In a preferred embodiment, the prodrug comprises:

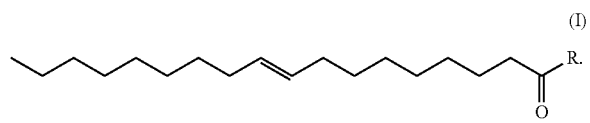

(I)

wherein, R is anticancer drug, the anticancer drug comprises gemcitabine, cytarabine, adriamycin, fluorouracil, and combinations thereof.

Representatively, the drug comprises gemcitabine elaidate.

Typically, the gemcitabine elaidate has the structure as follows:

In a preferred embodiment, the drug is loaded in the nanometer particle by one or more means selected from the group consisting of:
(i) the free drug is encapsulated into the nanometer particle; and/or
(ii) the drug is used as nanomaterial or lipid material in the form of amphiphilic prodrug.

Tumor

The tumor of the present invention is not particularly limited. For example, the tumor can be low permeability tumor or solid tumor.

Preferably, the tumor comprises low permeability solid tumor.

In a preferred embodiment, the tumor is selected from the group consisting of pancreatic cancer, glioma, and combinations thereof.

Representatively, the pancreatic cancer is pancreatic ductal adenocarcinoma.

Representatively, the pancreatic cancer is human pancreatic ductal adenocarcinoma.

Representatively, the glioma is cerebral glioma.

Representatively, the glioma is human cerebral glioma.

Nanometer Particle and Use Thereof

The nanometer particle of the present invention refers to micro particle in nanometer scale. For example, the particle size of the nanometer particle is 200-500 nm, preferably 300-450 nm, more preferably 330-400 nm, more preferably 360-400 nm, more preferably 370-390 nm.

In a preferred embodiment, the nanometer particle of the present invention is nanoparticle or liposome.

In a preferred embodiment, the nanometer particle of the present invention is nanoparticle. The nanoparticle is solid colloidal particle made of natural or synthetic polymer materials with a particle size of 0.1~100 nm.

In a preferred embodiment, the nanometer particle of the present invention is liposome. The liposome is a particle with a bilayer structure, and is similar to a cell membrane.

In a preferred embodiment, the amphiphilic material of the present invention is used as nanomaterial of the nanoparticle.

In a preferred embodiment, the nanoparticle further comprises other nanomaterials.

Preferably, the nanomaterial comprises amphiphilic nanomaterial.

Representatively, the other nanomaterials are selected from the group consisting of polyethylene glycol-polylactic acid (PEG-PLA).

In a preferred embodiment, the amphiphilic material is used as lipid material of the liposome.

Preferably, the liposome further comprises other lipid materials.

CP4126

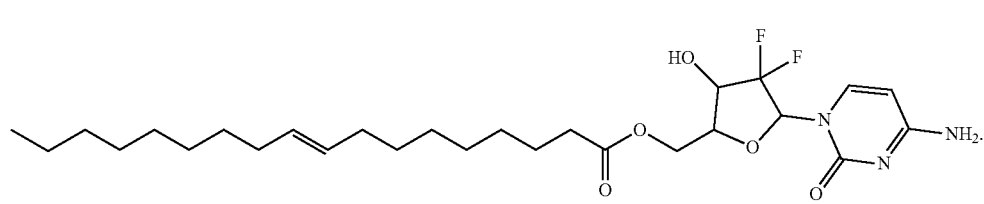

In a preferred embodiment, the liposome material comprises amphiphilic lipid material.

Representatively, the other lipid materials are selected from the group consisting of 1,2-dipalmitoyl-sn-glycero-3-phosphocholine (DPPC), 1,2-distearoyl-sn-glycero-3-phosphoethanolamine-polyethylene glycol (DSPE-PEG), 1,2-dioleoyl-sn-glycero-3-phosphoethanolamine (DOPE), soy bean phospholipid, phosphatidylcholine (PC, lecithin), cholesterol, phosphatidylethanolamine (PE, cephalin), phosphatidylserine (PS), phosphatidylinositol (PI), phosphatidylglycerol (PG), dicetyl phosphate (DCP), dimyristoylphosphatidylcholine (DMPC), distearoylphosphatidylcholine (DSPC), dilaurylphosphatidylcholine (DLPC), dioleoylphosphatidylcholine (DOPC), and combinations thereof.

Preferably, the 1,2-distearoyl-sn-glycero-3-phosphoethanolamine-polyethylene glycol (DSPE-PEG) is selected from the group consisting of DSPE-PEG600, DSPE-PEG800, DSPE-PEG1000, DSPE-PEG2000, DSPE-PEG4000, DSPE-PEG6000, and combinations thereof.

In a preferred embodiment, the nanometer particle is non drug-loaded or drug-loaded nanometer particle.

The present invention further provides a use of the nanometer particle of the present invention for loading drug.

In a preferred embodiment, the nanometer particle promotes the drug (e.g., anticancer drug) into tumor cell to enhance the killing effect of the drug on the tumor.

The present invention further provides a use of the drug-loaded nanometer particle of the present invention in the preparation of a composition for the prevention and/or treatment of disease.

In a preferred embodiment, the disease is an indication disease of the drug

Representatively, the disease comprises tumor.

In a preferred embodiment, the composition is a pharmaceutical composition.

Preferably, the pharmaceutical composition further comprises a pharmaceutically acceptable carrier.

Preferably, the composition is solid preparation, liquid preparation or semi-solid preparation.

Preferably, the composition is injection preparation, oral preparation or external preparation.

In a preferred embodiment, the injection preparation is intravenous injection preparation, intratumoral injection preparation, tumor intravascular injection preparation or tumor microenvironment injection preparation.

In a preferred embodiment, the treatment comprises inhibition, alleviation, relief, reversal or eradication.

Liposome, Preparing Method and Use Thereof

The nanometer particle of the present invention are preferably drug-loaded liposome. The liposome is a particle with a bilayer structure, and is similar to a cell membrane.

In a preferred embodiment, the liposome comprises lipid material and drug, the lipid material is used as lipid bilayer; the lipid material comprises 1,2-dipalmitoyl-sn-glycero-3-phosphocholine (DPPC), the amphiphilic material of the present invention and 1,2-distearoyl-sn-glycero-3-phosphoethanolamine-polyethylene glycol (DSPE-PEG).

In a preferred embodiment, the drug in the liposome of the present invention is prodrug.

In a preferred embodiment, the particle size of the liposome is 200-500 nm, preferably 300-450 nm, more preferably 330-400 nm, more preferably 360-400 nm, more preferably 370-390 nm.

In a preferred embodiment, the prodrug is used as lipid material of the liposome.

Preferably, the prodrug is used as lipid bilayer.

In a preferred embodiment, the 1,2-distearoyl-sn-glycero-3-phosphoethanolamine-polyethylene glycol (DSPE-PEG) is selected from the group consisting of DSPE-PEG600, DSPE-PEG800, DSPE-PEG1000, DSPE-PEG2000, DSPE-PEG4000, DSPE-PEG6000, and combinations thereof.

In a preferred embodiment, the liposome further comprises water, buffer solution and/or perfluoropentane.

In a preferred embodiment, the liposome encapsulates water, buffer solution and/or perfluoropentane.

Preferably, the lipid bilayer encapsulates water, buffer solution and/or perfluoropentane.

In a preferred embodiment, the buffer solution comprises glycerol-contained phosphate buffer saline.

Preferably, the volume fraction of the glycerol is 5-15%, preferably 8-12%, more preferably 10% in the glycerol-contained phosphate buffer saline.

Preferably, the concentration of the glycerol-contained phosphate buffer saline is 5-15 mM, preferably 8-12 mM, more preferably 10 mM, based on the concentration of phosphate radical.

Preferably, the pH of the glycerol-contained phosphate buffer saline is 7.2-7.6, preferably 7.4.

Preferably, the lipid bilayer encapsulates perfluoropentane and/or glycerol-contained phosphate buffer saline.

In a preferred embodiment, the weight ratio of the 1,2-dipalmitoyl-sn-glycero-3-phosphocholine (DPPC) to the amphiphilic material of the present invention is 0.2-2:0.2-2, preferably 0.5-1.5:0.5-1.5, more preferably 0.8-1.2:0.8-1.2, most preferably 1:1.

Preferably, the weight ratio of the 1,2-dipalmitoyl-sn-glycero-3-phosphocholine (DPPC) to the 1,2-distearoyl-sn-glycero-3-phosphoethanolamine-polyethylene glycol (DSPE-PEG) is 0.5-5:1, preferably 0.8-3:1, more preferably 1-2:1, more preferably 1.3-1.7:1, most preferably 1.5:1.

Preferably, the weight ratio of the amphiphilic material of the present invention to the 1,2-distearoyl-sn-glycero-3-phosphoethanolamine-polyethylene glycol (DSPE-PEG) is 0.5-5:1, preferably 0.8-3:1, more preferably 1-2:1, more preferably 1.3-1.7:1, most preferably 1.5:1.

Preferably, the weight ratio of the 1,2-dipalmitoyl-sn-glycero-3-phosphocholine (DPPC) to the prodrug is 0.5-5:1, preferably 0.8-3:1, more preferably 1-2:1, more preferably 1.3-1.7:1, most preferably 1.5:1.

Preferably, the weight ratio of the amphiphilic material of the present invention to the prodrug is 0.5-5:1, more preferably 0.8-3:1, more preferably 1-2:1, more preferably 1.3-1.7:1, most preferably 1.5:1.

Preferably, the weight ratio of the 1,2-distearoyl-sn-glycero-3-phosphoethanolamine-polyethylene glycol (DSPE-PEG) to the prodrug is 0.2-2:0.2-2, preferably 0.5-1.5:0.5-1.5, more preferably 0.8-1.2:0.8-1.2, most preferably 1:1.

Preferably, the mass volume ratio (mg:μl) of the 1,2-dipalmitoyl-sn-glycero-3-phosphocholine (DPPC) to the perfluoropentane is 1:20-50, preferably 1:20-40, more preferably 1:25-38, more preferably 1:30-35, more preferably 1:22-34.

Preferably, the mass volume ratio (mg: μl) of the amphiphilic material of the present invention to the perfluoropentane is 1:20-50, more preferably 1:20-40, more preferably 1:25-38, more preferably 1:30-35, most preferably 1:32-34.

Preferably, the mass volume ratio (mg:μl) of the 1,2-distearoyl-sn-glycero-3-phosphoethanolamine-polyethylene glycol (DSPE-PEG) to the perfluoropentane is 1:30-70, preferably 1:40-60, more preferably 1:45-55, more preferably 1:48-52.

Preferably, the volume ratio of the perfluoropentane to the buffer solution is 1:40-80, preferably 1:50-70, more preferably 1:55-65, more preferably 1:58-62.

Preferably, the volume ratio of the perfluoropentane to the glycerol-contained phosphate buffer saline is 1:40-80, preferably 1:50-70, more preferably 1:55-65, more preferably 1:58-62.

Specifically, the liposome of the present invention is as described in the fifth aspect of the present invention.

The present invention further provides a method for preparing the liposome of the present invention, which comprises the following steps:
(1) dissolving the lipid material and the prodrug in an organic solvent, and removing the organic solvent to obtain a lipid film;
(2) hydrating the lipid film with perfluoropentane and buffer solution, and stirring to obtain the liposome.

Preferably, in the step (1), the organic solvent is selected from the group consisting of chloroform, dichloromethane, and combinations thereof.

Preferably, the volume ratio of the perfluoropentane to the glycerol-contained phosphate buffer saline is 1:40-80, preferably 1:50-70, more preferably 1:55-65, more preferably 1:58-62.

Preferably, the method comprises the following steps:
(i) dissolving the DPPC, the amphiphilic material (DOPE-DMA) of the present invention, DSPE-PEG and gemcitabine elaidate in chloroform, and removing the solvent by rotary evaporation under reduced pressure to obtain the lipid film in round bottom flask;
(ii) cooling the lipid film to 2-6° C., and adding perfluoropentane to immerse the lipid film, then adding glycerol-contained phosphate buffer saline to hydrate, stirring for 0.8-1.2 h at 2-6° C., and then stirring for 0.8-1.2 h at 25-35° C. in the open round bottom flask to obtain the liposome.

Preferably, the method comprises the following steps:
(i) dissolving 1.2-1.8 mg of DPPC, 1.2-1.8 mg of the amphiphilic material (DOPE-DMA) of the present invention, 0.8-1.2 mg of DSPE-PEG and 0.8-1.2 mg of gemcitabine elaidate in chloroform, and removing the solvent by rotary evaporation under reduced pressure to obtain the lipid film in round bottom flask;
(ii) cooling the lipid film to 2-6° C., and adding 45-55 µL of perfluoropentane to immerse the lipid film, then adding 2.8-3.2 mL of glycerol-contained phosphate buffer saline to hydrate, stirring for 0.8-1.2 h at 2-6° C., and then stirring for 0.8-1.2 h at 25-35° C. in the open round bottom flask to obtain the liposome.

In a preferred embodiment, the method for preparing the liposome of the present invention is as described in the sixth aspect of the present invention.

The present invention further provides a use of the drug-loaded liposome of the present invention in the preparation of a composition for the prevention and/or treatment of disease.

In a preferred embodiment, the disease is an indication disease of the drug

Representatively, the disease comprises tumor.

In a preferred embodiment, the composition is a pharmaceutical composition.

Preferably, the pharmaceutical composition further comprises a pharmaceutically acceptable carrier.

Preferably, the composition is solid preparation, liquid preparation or semi-solid preparation.

Preferably, the composition is injection preparation, oral preparation or external preparation.

In a preferred embodiment, the injection preparation is intravenous injection preparation, intratumoral injection preparation, tumor intravascular injection preparation or tumor microenvironment injection preparation.

In a preferred embodiment, the treatment comprises inhibition, alleviation, relief, reversal or eradication.

System or Device

The present invention further provides a system or device for treating disease, the system or device comprises the nanometer particle or the liposome of the present invention; and an ultrasound device.

In a preferred embodiment, the system or device further comprises a label, the specification or label records that an ultrasound stimulation is carried out on the lesion site (e.g., tumor site) during the administration of the liposome of the present invention to a subject in need for the prevention and/or treatment of disease.

In a preferred embodiment, the ultrasound device comprises ultrasonic instrument.

In a preferred embodiment, the subject comprises human and non-human mammal.

In a preferred embodiment, the non-human mammal comprises cattle, horse, sheep, dog, cat or mouse.

In a preferred embodiment, the disease is an indication disease of the drug

In a preferred embodiment, the disease comprises tumor.

In a preferred embodiment, the administration is injection administration, oral administration or external administration.

In a preferred embodiment, the injection administration is intravenous injection administration, intratumoral injection administration, tumor intravascular injection administration or tumor microenvironment injection administration.

A Method for Preventing and/or Treating Disease

The present invention further provides a method for preventing and/or treating disease, which comprises administering the nanometer particle or the liposome of the present invention to a subject in need, thereby treating disease.

Preferably, the subject comprises human and non-human mammal.

Preferably, the non-human mammal comprises cattle, horse, sheep, dog, cat or mouse.

Preferably, the disease is an indication disease of the drug

Preferably, the disease comprises tumor.

Preferably, an ultrasound stimulation is carried out on the lesion site (e.g., tumor site) during the administration of the nanometer particle or the liposome of the present invention to a subject in need.

Preferably, the administration is injection administration, oral administration or external administration.

Preferably, the injection administration is intravenous injection administration, intratumoral injection administration, tumor intravascular injection administration or tumor microenvironment injection administration.

Composition

The composition of the present invention comprises but is not limited to pharmaceutical composition.

The composition of the present invention can further comprises a pharmaceutically acceptable carrier. The term "pharmaceutically acceptable carrier" refers to one or more compatible solid or liquid fillers or gel materials, which are suitable for use in human and must have sufficient purity and sufficiently low toxicity. The "compatible" means each ingredient of the composition and the compound of the present invention can be blended with each other without significantly reducing the efficacy. Some examples of the pharmaceutically acceptable carriers are cellulose and its derivatives (e.g. sodium carboxymethylcellulose, ethylcellulose, cellulose acetate, etc.), gelatin, talc, solid lubricants (e.g. stearic acid, magnesium stearate), calcium sulfate, plant oil (e.g. soybean oil, sesame oil, peanut oil, olive oil, etc.), polyols (e.g. propylene glycol, glycerin, mannitol, sorbitol, etc.), emulsifier (e.g. Tweed), wetting agent (e.g. sodium lauryl sulfate), colorant, flavoring agent, stabilizer, antioxidant, preservative, pyrogen-free water, etc.

The administration mode of the composition of the present invention has no special limitation. Representative mode of administration comprises but is not limited to injection administration, oral administration or external administration. Preferably, the injection administration is intravenous injection administration, intratumoral injection administration, tumor intravascular injection administration or tumor microenvironment injection administration.

The dosage form of the composition or preparation of the present invention is oral preparation, external preparation or injection preparation. Representatively, the solid dosage form used for oral administration comprises capsule, tablet, pill, powder and granule. In the solid dosage form, the active compound is mixed with at least one conventional inert excipient (or carrier), such as sodium citrate or dicalcium phosphate, or with the components as follows: (a) fillers or compatibilizers, such as starch, lactose, sucrose, glucose, mannitol and silicic acid; (b) binders, such as hydroxymethyl cellulose, alginate, gelatin, polyvinylpyrrolidone, sucrose and arabic gum; (c) humectants, such as glycerin; (d) disintegrants, such as agar, calcium carbonate, potato starch or cassava starch, alginic acid, some composite silicates, and sodium carbonate; (e) slow corrosion agents, such as paraffin; (f) absorption accelerators, such as quaternary amine compounds; (g) wetting agents, such as cetyl alcohol and glyceryl monostearate; (h) adsorbents, such as kaolin; and (i) lubricants, such as talc, calcium stearate, magnesium stearate, solid polyethylene glycol, sodium dodecyl sulfate, or mixtures thereof. In the capsule, tablet and pill, the dosage form can further contain a buffer.

The parenteral injection composition can comprise physiologically acceptable sterile aqueous or anhydrous solution, dispersion, suspension or emulsion, and sterile powders for redissolution into sterile injectable solution or dispersion. Suitable aqueous and non-aqueous carrier, diluent, solvent or excipient comprise water, ethanol, polyols and suitable mixtures thereof.

The dosage form of the compound of the present invention for topical application or administration comprises ointment, powder, patch, spray and inhalation. The active ingredient can be mixed with physiologically acceptable carrier and any preservative, buffers or propellant that can be needed when necessary under sterile condition.

The composition is administered by applying a safe and effective amount of the nanometer particle or liposome of the present application to a human or non-human animal (e.g., rat, mouse, dog, cat, cow, sheep, chicken, duck, etc.) in need, wherein the administration dose is a pharmaceutically acceptable effective amount. As used herein, the term "safe and effective amount" refers to an amount that has a function or activity in human and/or animal and is acceptable to human and/or animal. It should be understand in the art that the "safe and effective amount" can vary depending on the form of the pharmaceutical composition, the route of administration, the excipients of the drug, the severity of the disease, and the combination with other drugs, etc. For example, for a person with a body weight of 60 kg, the daily dosage is usually 0.1 to 1000 mg, preferably 1 to 600 mg, more preferably 2 to 300 mg. Of course, the specific dose should also take into account the route of administration, the patient's health and other factors, which are within the skill range of skilled doctors.

The Main Advantages of the Present Invention Comprise

1. The present invention develops an amphiphilic material with novel structure, the drug-loaded nanometer particle (e.g., drug-loaded liposome) prepared by the amphiphilic material can significantly and effectively enter tumor cells, thereby enhancing the anti-tumor therapeutic effect of the drug.
2. The drug-loaded nanometer particle (e.g., drug-loaded liposome) prepared by the amphiphilic material of the present invention has excellent long blood clearance half-life, can significantly expand or increase the opening in the vascular endothelial cells under ultrasound stimulation, promote the drug-loaded liposome to penetrate the tumor site from the blood vessels, significantly promote the drug-loaded liposome into the tumor cells, and avoid the retention and degradation of lysosomes, thereby enhancing the anti-tumor effect of drug.
3. The amphiphilic material of the present invention has good biocompatibility and high safety.

The present invention will be further illustrated below with reference to the specific examples. It should be understood that these examples give a detailed implementation mode and specific operation process based on the technical solution but are not to limit the scope of the invention Example 1

1. Materials and Instruments 1.1 Materials

All chemical reagents other than indicated were purchased from Sigma-Aldrich Inc. and Aladdin Reagent Inc. DOPE, DPPC, and DSPE-PEG2000 were purchased from Avanti Lipids Inc. (USA). Cyanine5 (Cy5)-labeled DSPE-PEG2000 (DSPE-PEG$^{Cy5}$) was purchased from Xi' an Ruixi Biological Technology Co. Ltd. EXO1 and gemcitabine prodrug CP4126 were purchased from Med-chem Express. RPMI 1640 culture medium, DMEM culture medium, fetal bovine serum (FBS) and 0.25% trypsin solution were purchased from GIBCO (USA). Alamar Blue Cell Viability Reagent, Hoechst 33342, and LysoTracker® Green DND26 were purchased from Thermo Fisher Scientific Inc. Ki67 antibody was purchased from Proteintech Group. TUNEL apoptosis Assay Kit was purchased from Roche. Matrigel basement membrane matrix was purchased from BD Biosciences.

The gemcitabine prodrug CP4126 was gemcitabine elaidate with the structure as follows:

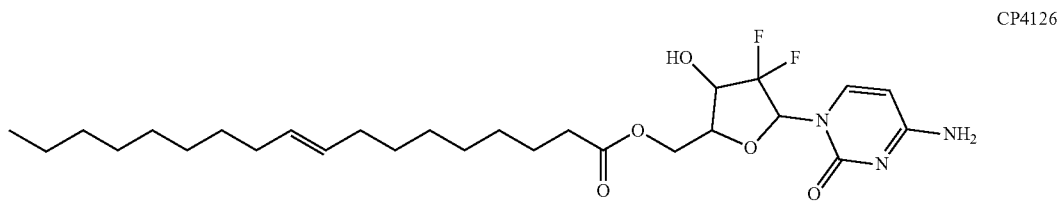 [SMILES: CCCCCCCC/C=C/CCCCCCCC(=O)OCC1OC(n2ccc(N)nc2=O)C(F)(F)C1O]

1.2 Instruments

The hydrodynamic diameter size (particle size) and zeta potential of the nanometer particle were measured by using a dynamic light scattering analyzer (Nano-ZS 90, Malvern). The refractive index of the nanometer particle was selected to be 1.59 to determine the particle size by intensity percent (intensity %).

The morphology of the nanometer particle was imaged by cryo-transmission electron microscope (cryo-TEM) (Talos F200C 200kv, FEI Inc.) in a carbon-coated 200-mesh copper TEM grid.

The fluorescence spectra and fluorescence intensity of Cy5-labeled nanometer particle were detected with a microplate reader (SpectraMax M5, Molecular Devices).

2. Cell Culture and Animal Model

Human pancreatic ductal adenocarcinoma (PDA) cell line BxPC3, human glioma cell line U251, human umbilical vein endothelial cells (HUVEC) were purchased from American Type Culture Collection. BxPC3 was cultured in RPMI 1640 culture medium. U251 and HUVEC were cultured in DMEM culture medium. Those culture mediums were supplemented with 10% FBS, penicillin (100 U/mL) and streptomycin (100 μg/mL) in a humidified atmosphere of 5% $CO_2$ at 37° C.

Male BALB/c mice (6-8 weeks) were supplied by the Laboratory Animal Center of Zhejiang Chinese Medical University. Mice were housed in approved animal-care facilities on a 12 h light/dark cycle and were free to food and water. The pancreatic tumor-bearing mouse model were established by subcutaneous or orthotopic inoculation with BxPC3 cells stably expressing luciferase (BxPC3-Luci). The glioma-bearing mouse model were established by subcutaneous inoculation with U251 cell line.

3. Synthesis of Lipid Materials

3.1 Synthesis of DOPE-DMA

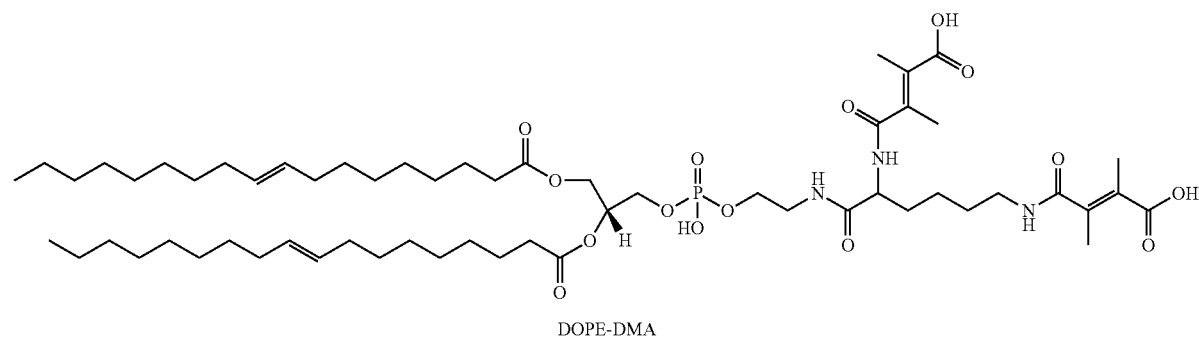 [SMILES: CCCCCCCC/C=C/CCCCCCCC(=O)OC[C@H](COP(=O)(O)OCCNC(=O)C(CCCCNC(=O)/C(C)=C(\C)C(=O)O)NC(=O)/C(C)=C(\C)C(=O)O)OC(=O)CCCCCCC/C=C/CCCCCCCC]

DOPE-DMA

Figure 2:
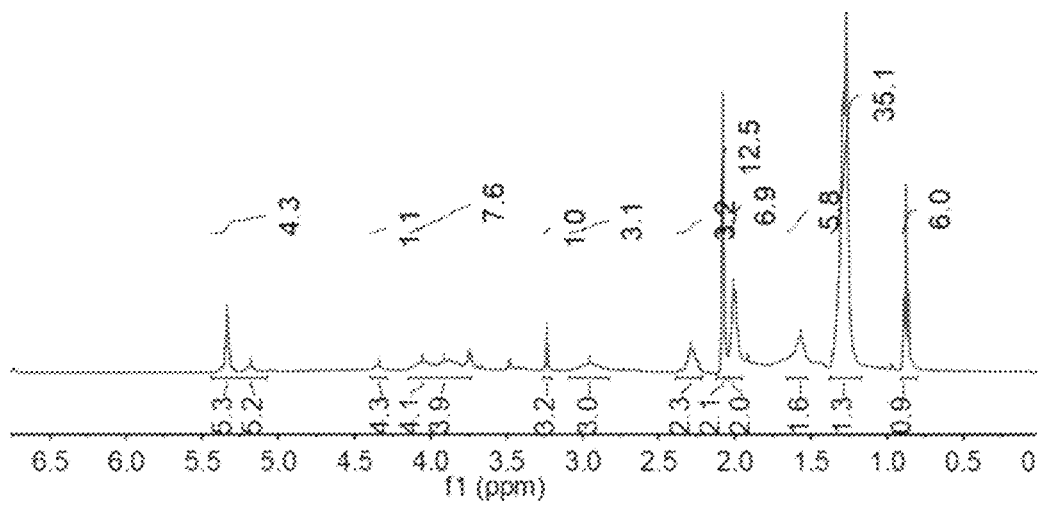
FIG. 2 shows the $^1$H-NMR of DOPE-DMA.
Figure 3:
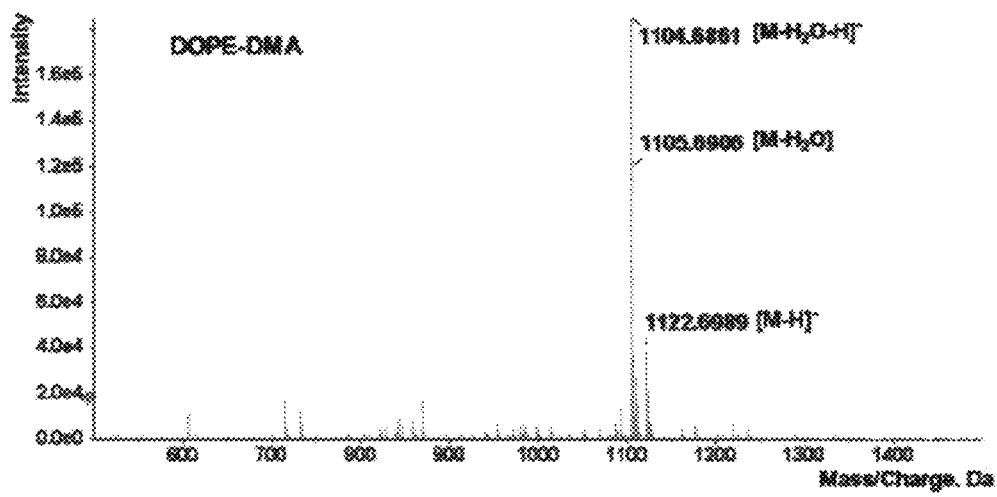
FIG. 3 shows the MALDI-TOF-MS spectrum of DOPE-DMA.

The synthesis route of DOPE-DMA was shown in FIG. 1, the specific steps were as follows:
(1) The synthesis of 1,2-Dioleoyl-sn-glycero-3-phosphoethanolamine-lysine(DOPE-Lys) Boc-protected lysine (Boc-Lys, 0.35 g, 1 mmol), 1-ethyl-(3-dimethylaminopropyl)carbodiimide hydrochloride (EDC, 0.39 g, 2 mmol) and N-hydroxysuccinimide (NHS, 0.23 g, 2 mmol) were mixed in dichloromethane (DCM, 10 mL) and reacted at room temperature for 4 h, and Dioleoyl phosphoethanolamine (DOPE, 0.75 g, 1 mmol) was added and reacted for 12 h at room temperature, then trifluoroacetic acid (TFA, 10 mL) was added and reacted at room temperature for 4 h. After concentrating by rotary evaporation, dialyzing (MWCO=500 Da) in methanol for 24 h, then drying by rotary evaporation, the DOPE-Lys was obtained (approximately 0.65 g, 74.5% yield).
(2) 2,3-dimethylmaleic anhydride (DMA, 0.15 g, 1.2 mmol), 4-dimethylaminopyridine (25 mg, 0.1 mmol) and DOPE-Lys (0.44 g, 0.5 mmol) were mixed in dichloromethane (5 mL) and stirred at room temperature for 12 h. After concentrating under reduced pressure, dialyzing (dialysis tube: MEMBRA-CEL MD44, MWCO=1000 Da, Viskase) in methanol, and lyophilizating, the DOPE-DMA was obtained (approximately 0.32 g, 57.2% yield). The $^1$H NMR and MALDI-TOF-MS spectra of DOPE-DMA were shown in FIG. 2 and FIG. 3 respectively:

$^1$H-NMR (400 MHz, CDC13, δ):

5.40-5.03 (m, 5H), 4.33 (s, 1H), 4.15-3.76 (m, 8H), 3.21 (s, 1H), 3.01 (s, 4H), 2.31 (s, 4H), 2.20-1.97 (s, 20H), 1.62 (s, 6H), 1.31 (m, 35H), 0.91 (s, 6H).

MALDI-TOF-MS:

The molecular weight of [M–H$_2$O–H]$^-$, [M–H$_2$O] and [M–H]$^-$ was 1104.68, 1105.69 and 1122.69.

3.2 Synthesis of DOPE-SA of round bottom flask, the solvent was removed by rotary evaporation under reduced pressure at 40° C., and a lipid film was obtained in the round flask.

(2) The lipid film was cooled to 4° C. and 50 μL of perfluoropentane was added to immerse the lipid film, and 3 mL of glycerol-contained phosphate buffer saline (10 mM, pH=7.4, the volume fraction of glycerol was 10 v/v %) was added for hydration, the mixture was stirred with magnetic stirrer at 4° C. for 1 h, then the mixture was stirred with magnetic stirrer at 30° C. for 1 h in open round bottom flask in water bath, and the SCGLN liposome nanodroplet was obtained, the encapsulation efficiency of gemcitabine was 100%, and the drug loading was 9.98 wt %.

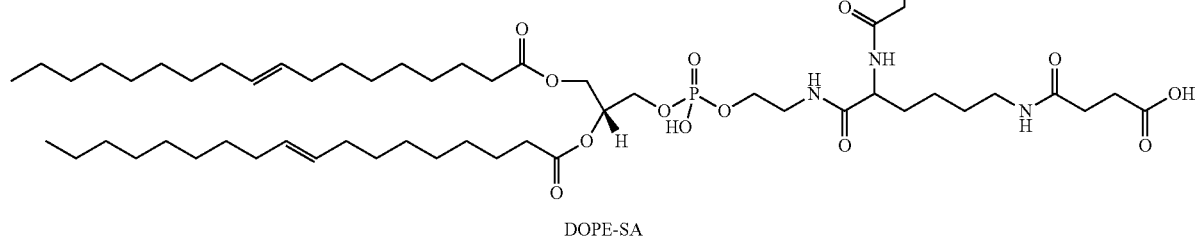

DOPE-SA

Figure 4:
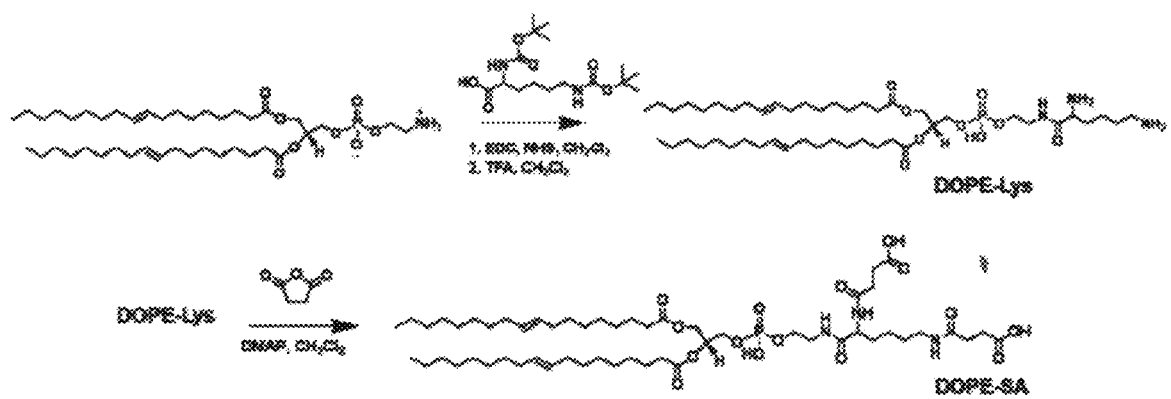
FIG. 4 shows the synthesis route of DOPE-SA.
Figure 5:
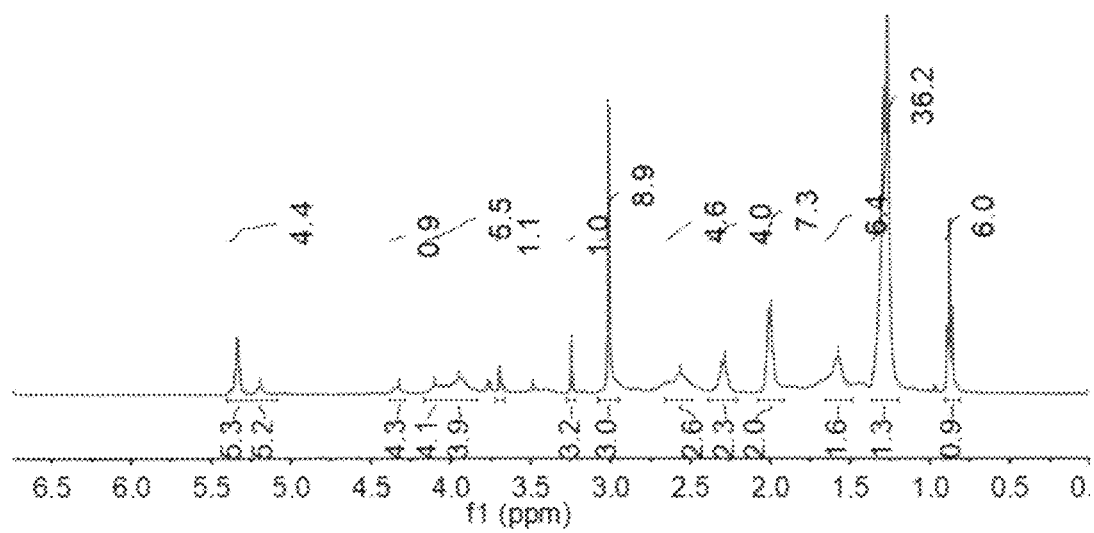
FIG. 5 shows the $^1$H-NMR of DOPE-SA.
Figure 6:
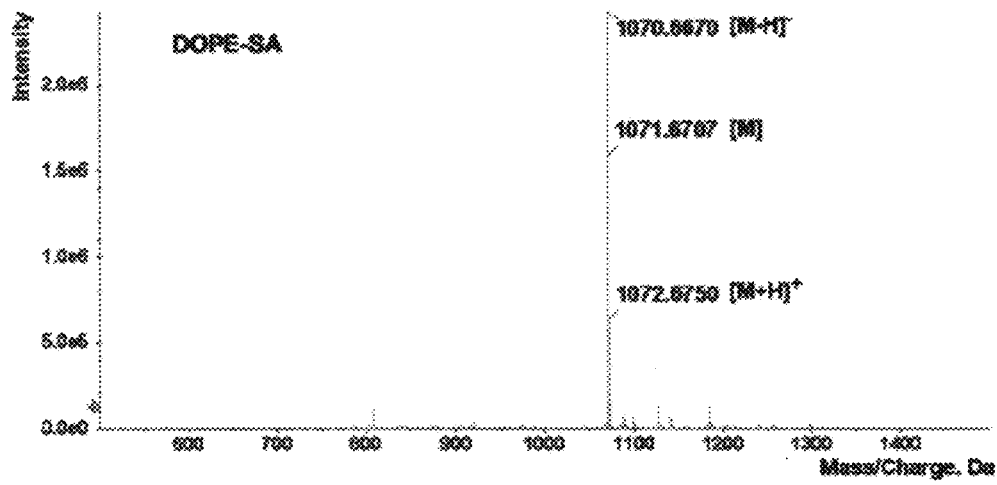
FIG. 6 shows the MALDI-TOF-MS spectrum of DOPE-SA.

The synthesis route of DOPE-SA was shown in FIG. 4, the specific steps were as follows:

Succinic anhydride (SA, 0.12 g, 1.2 mmol), 4-dimethylaminopyridine (25 mg, 0.1 mmol) and DOPE-Lys (0.44 g, 0.5 mmol) were mixed in dichloromethane (5 mL) and stirred at room temperature for 12 h. After concentrating under reduced pressure, dialyzing (dialysis tube: MEMBRA-CEL MD44, MWCO=1000 Da, Viskase) in methanol, and lyophilizating, the DOPE-SA was obtained. The $^1$H NMR and MALDI-TOF-MS spectra of DOPE-SA were shown in FIG. 5 and FIG. 6 respectively:

$^1$H-NMR (400 MHz, CDC13, δ):

5.38-5.01 (m, 5H), 4.30 (s, 1H), 4.12-3.77 (m, 7H), 3.22 (s, 1H), 3.01 (s, 9H), 2.62 (m, 5H), 2.36 (s, 4H), 2.02 (s, 8H), 1.61 (s, 6H), 1.32 (m, 36H), 0.90 (s, 6H).

MALDI-TOF-MS:

The molecular weight of [M–H]$^-$, [M] and [M+H]$^+$ was 1070.66, 1071.67 and 1072.67 respectively.

4. Preparation and Characterization of Liposome

4.1 Preparation of Liposome

4.1.1 Preparation of SCGLN Liposome Nanodroplet (1) 1.5 mg of DPPC, 1.5 mg of DOPE-DMA, 1 mg of DSPE-PEG2000 and 1 mg of gemcitabine prodrug CP4126 were dissolved in 2 mL of chloroform in a 5 ml

4.1.2 Preparation of Cy5-Labeled SCGLN Liposome Nanodroplet (SCGLN$^{CY5}$)

The preparation of SCGLN$^{CY5}$ was similar to "4.1.1 Preparation of SCGLN liposome nanodroplet", the difference was that the 1.5 mg of DSPE-PEG2000 was replaced with 1.5 mg of DSPE-$^{CY5}$.

4.1.3 Preparation of SGLN Liposome Nanodroplet (1) 1.5 mg of DPPC, 1.5 mg of DOPE-SA, 1 mg of DSPE-PEG2000 and 1 mg of gemcitabine prodrug CP4126 were dissolved in 2 mL of chloroform in a 5 ml of round bottom flask, the solvent was removed by rotary evaporation under reduced pressure at 40° C., and a lipid film was obtained in the round flask.

(2) The lipid film was cooled to 4° C. and 50 μL of perfluoropentane was added to immerse the lipid film, and 3 mL of glycerol-contained phosphate buffer saline (10 mM, pH=7.4, the volume fraction of glycerol was 10 v/v %) was added for hydration, the mixture was stirred with magnetic stirrer at 4° C. for 1 h, then the mixture was stirred with magnetic stirrer at 30° C. for 1 h in open round bottom flask in water bath, and the SGLN liposome nanodroplet was obtained, the encapsulation efficiency of gemcitabine was 100%, and the drug loading was 9.98 wt %.

4.1.4 Preparation of Cy5-Labeled SGLN Liposome Nanodroplet (SGLN$^{CY5}$)

The preparation of SGLN$^{CY5}$ was similar to "4.1.3 Preparation of SGLN liposome nanodroplet", the difference was that the 1.5 mg of DSPE-PEG2000 was replaced with 1.5 mg of DSPE-PEG$^{CY5}$.

4.1.5 Preparation of SCLN Liposome Nanodroplet (1) 1.5 mg of DPPC, 1.5 mg of DOPE-DMA and 1 mg of DSPE-PEG2000 were dissolved in 2 mL of chloroform in a 5 ml of round bottom flask, the solvent was removed by rotary evaporation under reduced pressure at 40° C., and a lipid film was obtained in the round flask.

(2) The lipid film was cooled to 4° C. and 50 μL of perfluoropentane was added to immerse the lipid film, and 3 mL of glycerol-contained phosphate buffer saline (10 mM, pH=7.4, the volume fraction of glycerol was 10 v/v %) was added for hydration, the mixture was stirred with magnetic stirrer at 4° C. for 1 h, then the mixture was stirred with magnetic stirrer at 30° C. for 1 h in open round bottom flask in water bath, and the SCLN liposome nanodroplet was obtained.

4.2 Characterization of Liposome Nanodroplets 4.2.1 The particle size of the liposome was measured with a dynamic light scattering analyzer (Nano-ZS 90, Malvern) at 37° C. after the liposome nanodroplet was appropriately diluted with PBS buffer saline solution (pH 7.4 or 6.5). The particle size of SCGLN or SGLN liposome nanodroplet in PBS buffer saline solution (pH 7.4) at 37° C. was shown in Table 1, and the image of the cryo-transmission electron microscope of SCGLN was shown in FIG. 7A of the FIG. 7.

TABLE 1

Particle size of the liposome in PBS buffer saline solution (pH 7.4) at 37° C. (unit: nm)

| Liposome | Particle size (nm) |
| --- | --- |
| SCGLN | 377.7 ± 60.2 |
| SGLN | 345.5 ± 53.8 |

The FIG. 7A showed that a distinct ice-cloud shadow was within the SCGLN liposome nanodroplet, indicating that the perfluoropentane was encapsulated into the SCGLN liposome nanodroplet.

Figure 7:
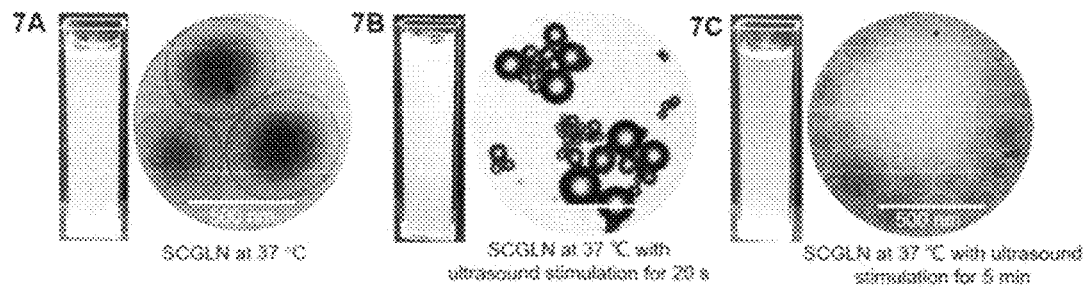
FIG. 7 shows the physicochemical properties of liposome nanodroplet. (7A) Cryo-transmission electron microscopy image of SCGLN liposome nanodroplet in PBS solution (pH7.4) at 37° C. (7B) Cryo-transmission electron microscopy image of SCGLN liposome nanodroplet after ultrasound stimulation for 20 s in PBS solution (pH7.4) at 37° C. (7C) Cryo-transmission electron microscopy image of SCGLN liposome nanodroplet after ultrasound stimulation for 5 min in PBS solution (pH7.4) at 37° C.

4.2.2 The change of the particle size of SCGLN or SGLN liposome nanodroplet treated with 20 s or 5 min ultrasound stimulation (intensity: 2 W/cm$^2$, frequency: 3 MHz, duty cycle: 50%) in PBS buffer saline solution (pH 7.4) at 37° C. was shown in Table 2, the image of the cryo-transmission electron microscopy of SCGLN at different ultrasound times were shown in FIG. 7B and FIG. 7C of the FIG. 7.

TABLE 2

The change of the particle size of the liposome treated with ultrasound stimulation at 37° C. (unit: nm)

| Ultrasound time | SGLN | SCGLN |
| --- | --- | --- |
| 20 s | 1806.5 ± 306.7 | 1574.7 ± 345.1 |
| 5 min | 202.1 ± 49.8 | 179.3 ± 27.6 |

The Table 1 and Table 2 showed that the particle size of SCGLN liposome nanodroplet was 377.7±60.2 nm in PBS buffer saline solution (pH 7.4) (simulating human blood environment) at 37° C. The particle size of SCGLN liposome nanodroplet became larger after ultrasound stimulation, and SCGLN liposome nanodroplet with particle size of 377.7±60.2 nm transformed into microbubble with the particle size of about 1.5 μm, and the microbubble broke and reassembled into nanoliposome (179.3 ±27.6 nm) with the increase of ultrasound time, indicating the microbubble was transformed into nanoliposome again. The SGLN and SCGLN had similar particle size transformation characteristic.

4.3 Characterization of Liposome Nanodroplet 4.3.1 Transport Across Blood Endothelial Cells A Transwell system (3 μm microporous polyester membrane and 24 mm diameter inserts) was used to investigate the transport of liposomes in endothelial cells. HUVEC endothelial cells (5×105 cells/mL, 1 mL) were incubated in the apical compartment for 4 days to facilitate the formation of a dense cell layer. BxPC3 cells (1×105 cells/mL, 1 mL) were seeded onto the basolateral compartment for 12 h. After placing the apical compartment onto the basolateral compartment, SCGLN$^{Cy5}$ or SGLN$^{Cy5}$ with the same GEM equivalent were added into the apical compartment with or without ultrasound stimulation (intensity: 2 W/cm$^2$, frequency: 3 MHz, duty cycle: 50%, duration: 5 min) and incubated for 2 h in the pH 7.4 or 6.5 culture medium. The fluorescence intensity of the basolateral culture medium was measured using a microplate reader. The BxPC3 cells were collected and measured in terms of Cy5 fluorescence intensity by flow cytometry.

Figure 8:
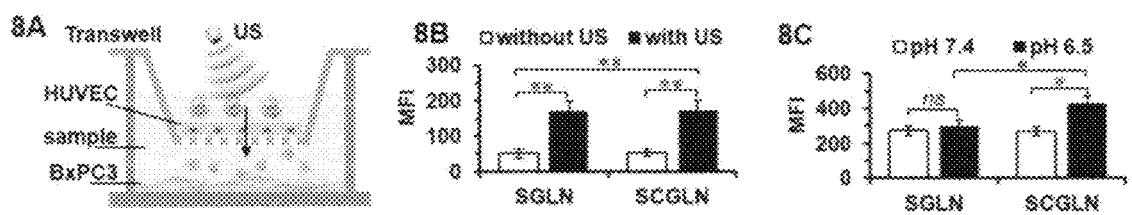
FIG. 8 shows the transvascular endothelial cell transport of different liposome nanometer particles. (8A) Transwell model for studying vascular permeability under ultrasound stimulation (US). (8B) Mean fluorescence intensity (MFI) of SCGLN$^{CY5}$ and SGLN$^{CY5}$ in the basolateral compartment through HUVEC blood vessel in pH7.4 medium at 37° C. with or without ultrasound stimulation in the Transwell model. (8C) Mean fluorescence intensity (MFI) of SGLN$^{CY5}$ and SGLN$^{CY5}$ in BxPC3 cell incubated for 1 h in pH7.4 or pH 6.5 medium of the basolateral compartment at 37° C. after ultrasound stimulation in the Transwell model

The FIG. 8 showed the Transwell model as shown in FIG. 8A was used to study the in vitro vascular permeability of different liposome nanometer particles treated with ultrasound stimulation. The vascular endothelial cells HUVEC were cultured in the apical compartment and the BxPC3 tumor cells were cultured in the basolateral compartment in the Transwell model. The FIG. 8B showed the MFI of SCGLN and SGLN treated with ultrasound stimulation (intensity: 2 W/cm$^2$, frequency: 3 MHz, duty cycle: 50%, duration: 5 min) was 3-4 times higher than the MFI of SCGLN and SGLN without ultrasound stimulation, indicating that the vascular permeability of SCGLN and SGLN was significantly enhanced under ultrasound stimulation. The FIG. 8C showed the SCGLN could significantly entry BxPC3 cells compared with SGLN in the acidic pH 6.5 culture medium (simulating the acidic tumor microenvironment), thus exerting the anticancer effect of anticancer gemcitabine (GEM) loaded in the SCGLN on tumor cells.

4.3.2 Cytotoxicity and Apoptosis Test

Figure 9:
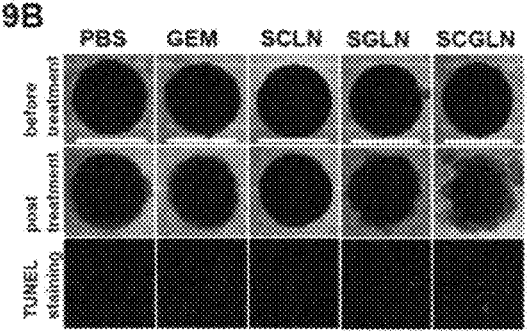
FIG. 9 shows cytotoxicity and apoptosis test. (9A) The IC$_{50}$ value of the cytotoxicity of GEM, SCGLN and SGLN liposome nanometer particle on 3D spheroid cultured BxPC3 cells in pH 6.5 culture medium at 37° C. after ultrasound stimulation. (9B) The cell morphology observed by light microscope and corresponding apoptosis analysis observed by TUNEL staining of 3D spheroid of BxPC3 treated with GEM or different liposome nanometer particles (all equivalent to 0.1 M GEM) for 72 h in pH 6.5 medium at 37° C. after ultrasound stimulation, the scale=500 μm.

The tumor spheroids were established using the hanging drop method. SCGLN, SGLN and free gemcitabine (GEM) were added into the wells at the final testing concentrations (equivalent to GEM: 0~10 μg/ml) at pH 6.5 culture medium with ultrasound stimulation (intensity: 2 W/cm$^2$, frequency: 3 MHz, duty cycle: 50%, duration: 5 min) and incubated for 72 h. Meanwhile, the SCLN was used as a control. Then the culture medium was replaced with a mixture of 90 μL fresh culture medium and 10 μL Alamar Blue Cell Viability Reagent and was continuously incubated for 12 h. The sample plates were then detected using a plate reader (SpectraMax $M_5$, Molecular Devices) to obtain fluorescence intensity readouts. The results of the cytotoxicity and apoptosis test were shown in FIG. 9.

The FIG. 9A showed the SCGLN had the strongest cytotoxicity in BxPC3 cells on 3D multicellular tumor spheroid with an $IC_{50}$ of 0.17 μM, which was 3-7 times higher than the cytotoxicity of GEM and SGLN.

Furthermore, the FIG. 9B showed the morphology of tumor spheres changed from a smooth sphere to a very irregular and collapsed shape after the BxPC3 cells on 3D multicellular tumor spheroid were inhibited by the SCGLN, and the corresponding apoptosis analysis observed by TUNEL staining showed the apoptotic cells caused by the SCGLN were distributed in the whole sphere, indicating that the SCGLN had excellent cytotoxicity.

4.3.3 Penetration in Tumor Spheroid

Figure 10:
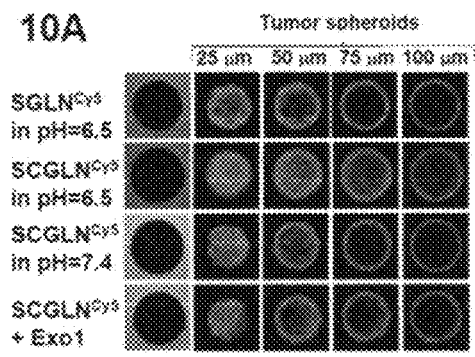
FIG. 10 shows the penetration results in 3D multicellular tumor spheroid of BxPC3. (10A) The tumor penetration of different liposome nanometer particles in 3D spheroid of BxPC3 cells in pH7.4 or pH 6.5 culture medium and the tumor penetration pretreated with exocytosis inhibitor EXO1 after ultrasound stimulation. (10B) The subcellular distribution of SCGLN in BxPC3 cells incubated for 3 h in pH 6.5 culture medium at 37° C. after ultrasound stimulation, nucleus (blue) is stained with Hoechst33342, lysosome (green) is stained with LysoTracker® GreenDND26, SCGLN is labeled with Cy5 (red), the scale=25 μm.
Figure 10:
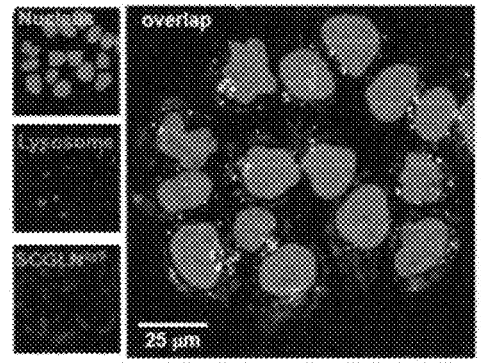

The three-dimensional (3D) multicellular tumor spheroid of BxPC3 were established and transferred to a confocal dish. $SCGLN^{CY5}$ or $SGLN^{CY5}$ (equivalent to the same GEM) were added at pH 6.5 or 7.4 culture medium with ultrasound stimulation (intensity: 2 W/cm², frequency: 3 MHz, duty cycle: 50%, duration: 5 min) and incubated for 6 h at 37° C. After washing with PBS, images were obtained with CLSM in XYZ-3D-stack at 25-μm intervals from apex to equator. Meanwhile, the tumor spheroid was pretreated with an exocytosis inhibitor EXO1 (20 μM) for 3 h to characterize exocytosis activity. The results of the penetration in tumor spheroid were shown in FIG. 10.

The FIG. 10A showed after incubation for 6 h in the pH 6.5 culture medium (simulating the acidic tumor microenvironment), the SGLN was mainly located at the periphery of BxPC3 sphere, while the SCGLN penetrated BxPC3 sphere and was distributed throughout the BxPC3 sphere. After incubation for 6 h in the pH 7.4 culture medium, or the pH 6.5 culture medium pretreated with exocytosis inhibitor EXO1, the SCGLN was located at the periphery of BxPC3 sphere, indicating the acidic microenvironment of tumor could promote the SCGLN into tumor cell via endocytosis, thus exerting the anticancer effect of anticancer drug loaded in the SCGLN.

The FIG. 10B showed the SCGLN was mainly distributed in the cytoplasm but not in the lysosome, indicating that the SCGLN could avoid the retention and degradation of the lysosome, thus effectively enhancing the anticancer effect of anticancer drug in cells.

4.3.4 Biodistribution, Penetration and In Vivo Imaging

Figure 11:
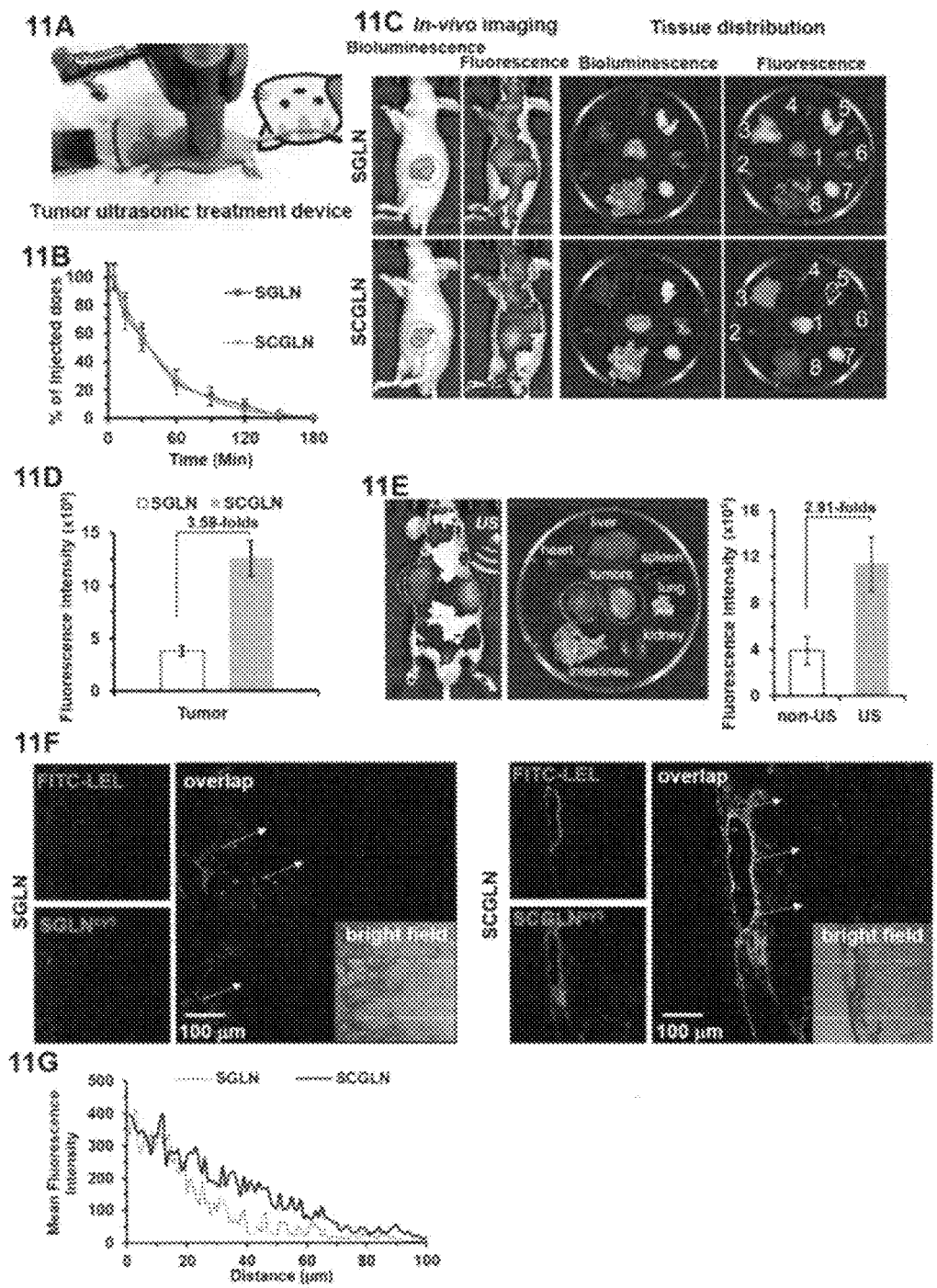
FIG. 11 shows the in vivo distribution, penetration and vivo imaging of liposome nanometer particles intravenously injected in BxPC3 xenograft mice. (11A) Ultrasound stimulation device is used for tumor treatment, ultrasound stimulation (intensity: 2 W/cm$^2$, frequency: 3 MHz, duty cycle: 50%) is performed for 10 min after the injection of Cy5-labeled liposome nanometer particles. (11B) Blood clearance curve of different nanometer particles injected intravenously. (11C) Bioluminescence and fluorescence images of mice and its excised tissues (1 represents tumor, 2 represents heart, 3 represents liver, 4 represents spleen, 5 represents lung, 6 represents kidney, 7 represents brain, and 8 represents small intestine) after intravenous injection of different Cy5-labeled liposome nanometer particles for 8 h. (11D) Quantification analysis of fluorescence intensity in the excised tumor of the Fig. C by using Living Image®-4.5 software. (11E) The in vivo fluorescence imaging and bio-distribution of Cy5-labeled SCGLN in BxPC3 tumor-bearing mice with tumors in right flank (with ultrasound stimulation) and left flank (without ultrasound stimulation). (11F) The penetration of different liposome nanometer particles in tumor. After the blood vessel staining in vivo with FITC-LEL and heart perfusion, the tumor was excised, frozen and cut into 10 μM thick slice, and visualized by CLSM imaging. (11G) The average fluorescence intensity gradient from the blood vessels to deep tumor parenchyma in the selected regions shown by white arrows in FIG. 11F.

Mice bearing orthotropic BxPC3 pancreatic tumor were used to investigate the accumulation and penetration of the drug in tumor. The mice were intravenously injected with the $SCGLN^{CY5}$ or $SGLN^{CY5}$ (dose equivalent to GEM 20 mg/kg, 3 mice in each group) and the orthotropic pancreas was treated with ultrasound stimulation (intensity: 2 W/cm, 3 MHz, duty cycle: 50%, duration: 10 min, Mettler Sonicator-740). Whole-body optical imaging was performed at 8 h of post-injection on a fluorescent spectral imager of Caliper IVIS Lumina II (PerkinElmer, USA) equipped with fluorescent filter sets (excitation/emission, 640/670 nm). Each mouse was then intravenously injected with FITC-labeled lycopersicon esculentum lectin (FITC-Lectin, 0.05 mg per mouse), and cardiac perfusion with 2% glutaraldehyde solution was performed after 5 min post-injection. The tumor tissues were then collected and frozen in Tissue OCT-Freeze Medium (Leica, Germany). After sectioning into 10 μm thick slices, images were photographed using CLSM and analyzed using Image J software. The results of biodistribution, penetration and in vivo imaging of the liposome nanodroplet injected intravenously into the BxPC3 xenotransplantation mice were shown in FIG. 11.

FIG. 11A showed the ultrasound device was used to perform ultrasound stimulation on orthotropic pancreas of the tumor-bearing mouse, the ultrasound probe (model: 1 cm², Sonicator 740) was stuck near the abdominal pancreas with medical ultrasound coupling agent. After intravenous injection of different liposome nanometer particles, ultrasound stimulation (intensity: 2 W/cm², frequency: 3 MHz, duty cycle: 50%) was performed immediately. The FIG. 11B showed the SCGLN and SGLN had similar long-time blood clearance with a clearance half-life of about 42 min, which was significantly higher than the blood clearance half-life of clinically commercially available ultrasound contrast agent (SonoVue, Sonazoid, etc., $T_{1/2}$ was from 5 to 20 min). The longer clearance half-life could significantly prolong the circulation time of SCGLN in blood, enhance the penetration of SCGLN into tumor site after ultrasound stimulation, and exert anti-tumor effects.

The FIG. 11C and FIG. 11D showed the SCGLN and SGLN as shown in the FIG. 11B had similar blood clearance and were cleared in the blood within about 2 h. However, the SCGLN showed higher tumor accumulation rate compared to the SGLN. The fluorescence intensity of SCGLN in the tumor was 3.59 times higher than that of SGLN, indicating that the SCGLN could effectively accumulate at tumor sites.

The biodistribution of the SCGLN was further studied in orthotropic BxPC3 tumo-bearing mice with two inoculated tumors on the right flank (with ultrasound stimulation) and left flank (without ultrasound stimulation), which eliminated individual mouse differences. The FIG. 11E showed the fluorescence intensity of tumor in the right flank with ultrasound stimulation was 2.91 times higher than that of tumor in the left flank without ultrasound stimulation, indicating that the ultrasound stimulation could enhance the accumulation of SCGLN in tumor.

The fluorescence co-localization of blood vessels and particles was used to study the tumor penetration of different liposome nanometer particles. As seen in FIG. 11F, the vessels stained with fluorescein isothiocyanate (FITC)-labeled lycopersicon esculentum lectin (FITC-Lectin) showed the SGLN was mostly located near the blood vessels, while the SCGLN could reach locations away from the vessels and be distributed deeply into the tumor parenchyma. The FIG. 11G showed the fluorescence intensity of SGLN decreased rapidly from blood vessels to deep tumor parenchyma and could not be detected beyond 70 μm, while the fluorescence intensity of SCGLN could be detected at a distance of 100 μm, indicating the SCGLN had excellent tumor penetration ability.

4.3.5 In Vivo Real-Time Vascular Extravasation Under Ultrasound Stimulation

Figure 12:
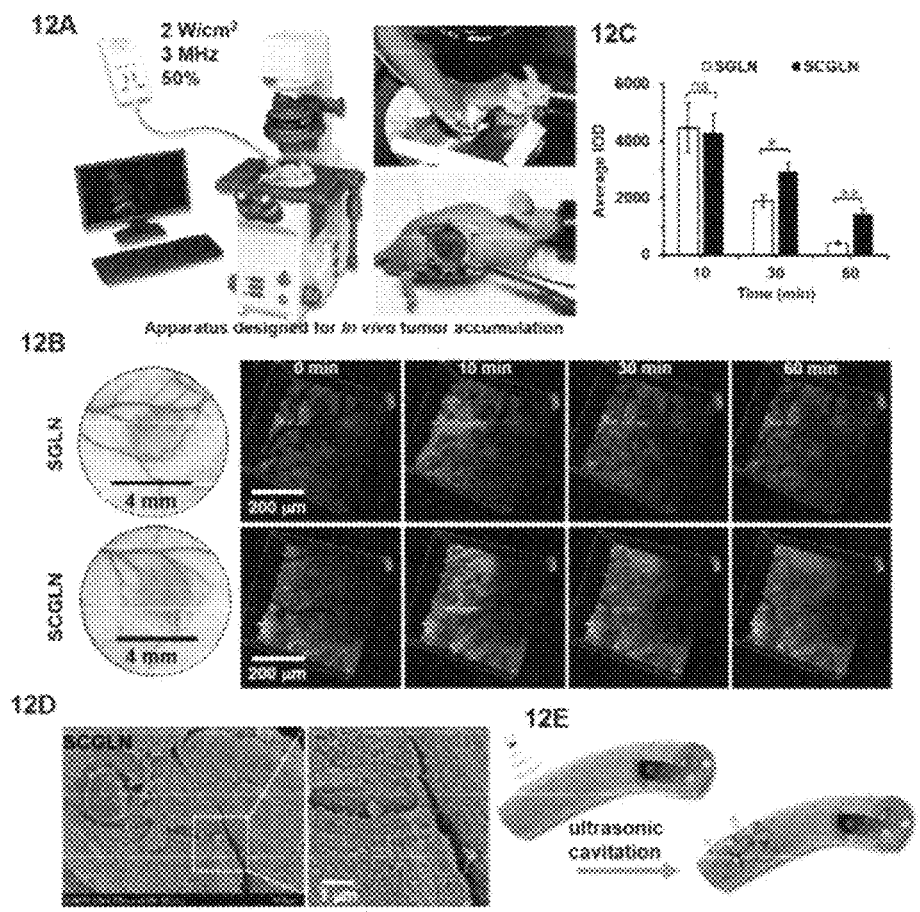
FIG. 12 shows the in vivo real-time tumor accumulation and vascular extravasation of SGLN$^{CY5}$ or SGLN$^{CY5}$ liposome nanometer particle intravenously injected after ultrasound stimulation. (12A) The imaging device is assembled with CLSM and ultrasound equipment. After different Cy5-labeled liposome nanometer particles are injected into the tail vein, ultrasound stimulation (intensity: 2 W/cm$^2$, frequency: 3 MHz, duty cycle: 50%). is performed at the tumor site for 10 min (12B) The in vivo real-time tumor accumulation and penetration of SGLN$^{CY5}$ or SGLN$^{CY5}$ liposome nanometer particle from the blood vessels to the tumor region at different times after the tail vein injection of SGLN$^{CY5}$ or SGLN$^{CY5}$ liposome nanometer particle. (12C) Quantitative analysis of the integrated optical density (IOD) of fluorescence of the injected SGLN$^{CY5}$ or SGLN$^{CY5}$ liposome nanometer particle at 10, 30 and 60 min in FIG. 12B. (12D) The ultrastructure of tumor vessels observed and analyzed by SEM at 60 min in FIG. 12B after the injection of SGLN$^{CY5}$ liposome nanometer particle. (12E) The simulated schematic diagram of SCGLN tumor accumulation induced by ultrasound stimulation based on SEM observation.

The mice were subcutaneously inoculated BxPC3 tumor beside the abdominal blood vessel. Once the tumor reached a size of 30-50 mm³, the tumor was fixed on a microscope slide using a dorsal skinfold chamber (APJ Trading Co. Inc, USA). The ultrasonic probe was fitted on the dorsal skinfold chamber with smearing the coupling agent. After the $SCGLN^{CY5}$ or $SGLN^{CY5}$ (dose equivalent to GEM 20 mg/kg) were intravenously injected, the tumor site was treated with ultrasound stimulation (intensity: 2 W/cm², 3 MHz, duty cycle: 50%, duration: 10 min, Mettler Sonicator-740). At 10 min, 30 min and 60 min after tail vein injection of $SCGLN^{CY5}$ or $SGLN^{CY5}$, the tumor region was imaged by using CLSM, and the corresponding fluorescence intensity of tumor was calculated by using Image J software. At 60 min after tail vein injection of $SCGLN^{CY5}$ or $SGLN^{CY5}$, cardiac perfusion was performed on the mice. The tumors were cut into small fragments and immersed in potassium hydroxide solution (30%) at 60° C. for 10 min. The samples were then stained by 2% tannin and 1% osmic acid for 2 h, dehydrated by ethanol and transferred into isoamyl acetate for critical point drying. After gold spraying treatment, the samples were observed in a field emission scanning electron microscope (SEM) (Hitachi Ltd, SU8010). The FIG. 12 showed the in vivo real-time tumor accumulation and vascular extravasation of SCGLN$^{CY5}$ or SGLN$^{CY5}$ liposome nanometer particle injected intravenously after ultrasound stimulation The in vivo real-time tumor accumulation and vascular extravasation of SCGLN$^{CY5}$ or SGLN$^{CY5}$ liposome nanometer particle injected intravenously in tail vein after ultrasound stimulation was studied by using the imaging device assembled by CLSM and ultrasonic device as shown in FIG. 12A. The FIG. 12B and FIG. 12C showed the SGLN and SCGLN liposome nanometer particle reduced rapidly in the blood vessels after intravenous injection. However, although the SGLN exuded from the capillaries within 30 min, the SGLN hardly penetrated into the deep of tumor, a small amount of SGLN was distributed around the blood vessels, and most of SGLN returned to the blood and were cleared. In contrast, the SCGLN could rapidly exude from the capillaries and penetrate the tumor parenchyma within 60 min. Although the SCGLN and SGLN had similar blood clearance, the fluorescence signal of the SCGLN was much stronger than that of the SGLN in tumor, indicating the SCGLN had excellent vascular extravasation and tumor accumulation ability. The FIG. 12D showed the openings between tumor vascular endothelial cells widened to about 1 μm and were rich after the SCGLN injected was treated with ultrasound stimulation, thus promoting the penetration of the nanometer particle from capillaries to tumor site. Therefore, the SCGLN injected could penetrate into the tumor site by widening the openings between tumor vascular endothelial cells after ultrasound stimulation, the ultrasound stimulation of the SCGLN could enhance the widening of the gap and opening of vascular endothelial cells at the tumor site, and promote the penetration of the SCGLN from the intravascular to tumor site. The schematic diagram of the SCGLN tumor accumulation induced by ultrasound stimulation was shown in FIG. 12E.

4.3.6 In Vivo Antitumor Activity

Figure 13:
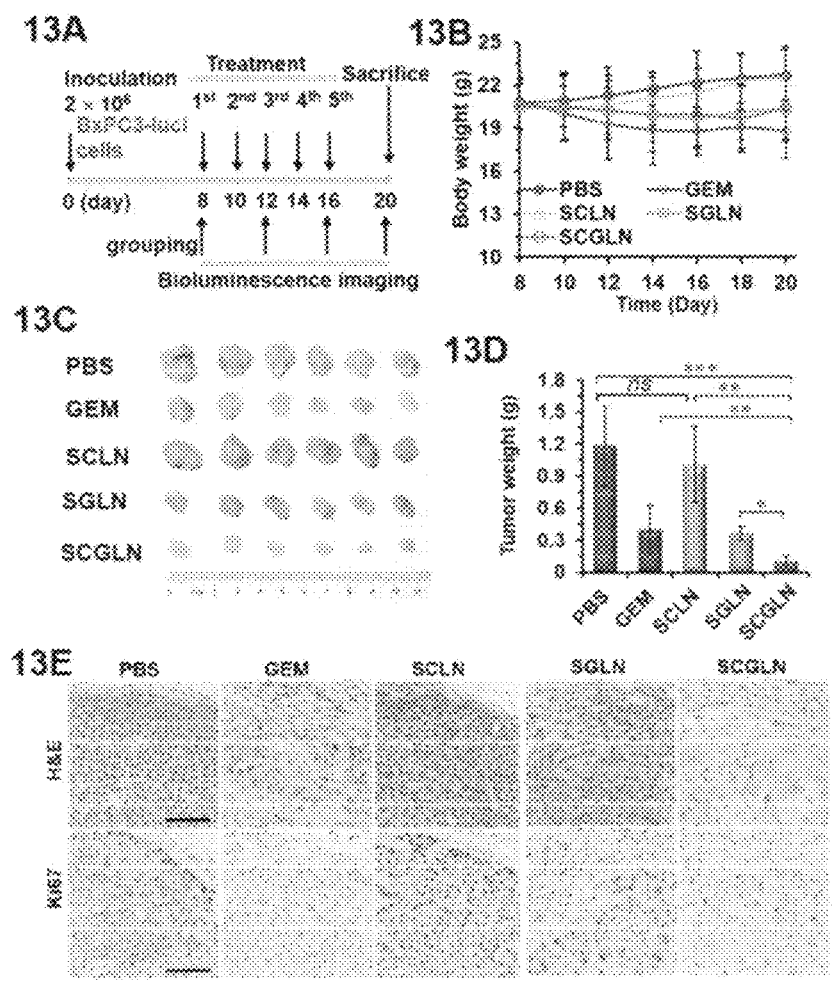
FIG. 13 shows the in vivo anti-tumor activity of different liposome nanometer particles in orthotropic BxPC3 tumor-bearing mice. (13A) The experimental and treatment schedule of each mouse inoculated with BxPC3-Luci cells. (13B) The body weight change of BxPC3-Luci tumor-bearing mice in different groups during the experiment. (13C) The photo of excised tumors at the end of the experiment. (13D) The mean tumor weight of each group at the end of the experiment. *: P<0.05: : P<0.01: *: P<0.001. (13E) Histological analysis of tumors stained with H&E and IHC of Ki67.

The orthotropic pancreatic tumor was established by using the bioluminescent BxPC3 cells (BxPC3-Luci). Bioluminescence intensities in mice were measured using the in vivo imaging system of Caliper IVIS Lumina II (PerkinElmer, USA) to evaluate tumour growth. After inoculation with bioluminescent BxPC3 cells for 8 days, the mice were selected and grouped into five groups (n=5). SCGLN, SGLN, free GEM (all dose equivalent to GEM 20 mg/kg), SCLN and PBS were intravenous injected every two days for a total of five times, the tumor site was treated with ultrasound stimulation (intensity: 2 W/cm$^2$, 3 MHz, duty cycle: 50%, duration: 10 min, Mettler Sonicator-740) after injection. On the first administration (8$^{th}$ day), 12$^{th}$, 16$^{th}$, and 20$^{th}$ day, tumor progress was assessed and semi-quantitatively analyzed via bioluminescence after injection of 10 mg/mL D-luciferin in PBS (200 μL) by using the in vivo imaging system. Mice were sacrificed on the 20$^{th}$ day, and tumors were dissected and weighed. The tumor inhibition rate=100%×(mean tumor weight of PBS group−mean tumor weight of experimental group)/mean tumor weight of PBS group. The tumors were fixed with 4% neutral buffered paraformaldehyde and embedded in paraffin. Tissue sections of 5-μm thick were mounted onto glass slides and stained with hematoxylin-eosin (H&E) and examined by light microscopy (OLYMPUS, BX51, Japan). Tissue sections were subjected to Ki67 staining using the Ki67-antibody Assay Kit (Proteintech, USA), the immunohistochemistry staining of Ki67 was tested to investigate the percentage of proliferous tumor cells positively stained in the examined field. The in vivo anti-tumor activities of different liposome nanometer particle on orthotropic BxPC3 tumor-bearing mice were shown in FIG. 13.

Figure 14:
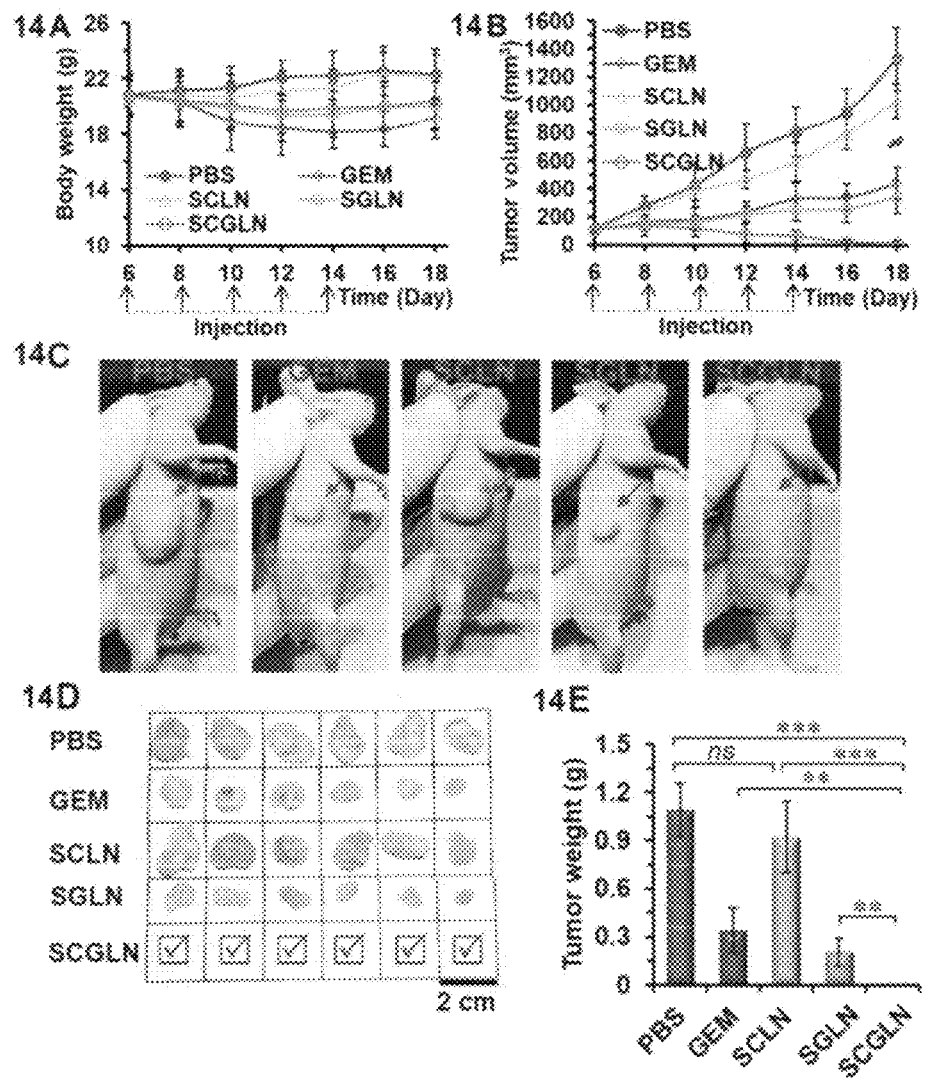
FIG. 14 shows the anti-tumor activity of different liposome nanometer particles in mice bearing U251 glioma subcutaneously. (14A) The weight change of U251 tumor-bearing mice in different groups during the experiment. (14B) The tumor volume change of U251 tumor-bearing mice in different group during the experiment. (14C) The tumor morphology of U251 tumor-bearing mice in different groups at the end of the experiment. (14D) The photo of excised tumors in U251 tumor-bearing mice of different groups at the end of the experiment. (14E) The average tumor weight of U251 tumor-bearing mice in different groups at the end of the experiment. *: P<0.05: : P<0.01: *: P<0.001.

In vivo antitumor activity of the liposomal nanometer particle was further tested in another low permeability tumor of U251 glioma. The mice were subcutaneously inoculated with 2×107 U251 cells on the right flank. Same as the experiment of pancreatic tumor treatment, mice were randomly grouped into five groups (n=5) on the 6$^{th}$ day after inoculation. SCGLN, SGLN, free GEM (all dose equivalent to GEM 20 mg/kg), SCLN and PBS were intravenous injected every two days for a total of five times, the tumor site was treated with ultrasound stimulation (intensity: 2 W/cm$^2$, 3 MHz, duty cycle: 50%, duration: 10 min, Mettler Sonicator-740) after injection, the first administration was on the 6$^{th}$ day. The width and length of the tumors and the bodyweight of mice were measured during the treatment. At the end of the experiment, the mice were euthanized, and tumors were dissected and weighed. The therapeutic efficacy of the treatments was evaluated by comparing the experimental group with the control group. The in vivo anti-tumor activities of different liposome nanometer particle on U251 glioma-bearing mice were shown in FIG. 14.

The FIG. 13A showed the experimental schedule and treatment schedule after each mouse was inoculated with BxPC3-Luci cells. The FIG. 13B showed the body weight of mice treated with SGLN and SCGLN decreased slightly but was not significant difference with the body weight of PBS, while the body weight of the mice treated with GEM decreased to nearly 10% of the initial weight at the end of the experiment, indicating that the SGLN and SCGLN had excellent biosafety. As seen in FIG. 13C and FIG. 13D, although the mean tumor weight of the SCLN was smaller than that of PBS buffer, there was no significant difference, indicating that the SCLN had no effect on tumor growth. The SCGLN had the strongest tumor inhibition ability in vivo with the mean tumor inhibition rate of 91.1%, which was much higher than that of GEM (66.7%), SCLN (14.4%) and SGLN (69.1%). Histological analysis of the tumor was performed to study the mechanism of anti-tumor activity. It could be seen from H&E staining in FIG. 13E that the density cells of the tumor treated with GEM, SGLN and SCGLN decreased compared with PBS treatment, and the tumor treated with the SCGLN contained a greater number of apoptotic cells, more extensive nuclear contraction and abundant cavities compared with GEM and SGLN. Ki67 immunostaining showed that Ki67 positive cells of the tumor treated with SCGLN were less than those treated with GEM and SGLN, indicating the SCGLN had significant inhibitory effect on the proliferation of tumor cells.

As could be seen in FIG. 14A, during the treatment, the weight of mice in the GEM group gradually decreased, while the weight of mice in the SGLN and SCGLN groups had no significant changes with no significant difference to PBS and SCLN groups. As could be seen in FIG. 14B and FIG. 14C, the GEM, SGLN and SCGLN had inhibitory effect on tumor compared with mice treated with PBS or SCLN. However, it was unexpectedly found the subcutaneous U251 glioma in the SCGLN group gradually decreased from the 4$^{rd}$ day after the first treatment and was completely eradicated and not visible on the 12$^{th}$ day after the first treatment. As could be seen in FIG. 14D and FIG. 14E, although the mean tumor weight of the SCLN was smaller than that of PBS buffer, there was no significant difference, indicating the SCLN had no effect on tumor growth. However, the SCGLN had excellent anti-tumor effect with 100% tumor eradication ability, better than GEM (68.8%) and SGLN (81.4%). The results showed that the SCGLN had excellent anti-tumor effect.

The above described is an embodiment of the present invention designed for a case. It should be understood that those skilled in the art will be able to make various changes or modifications without departing from the principle of the invention, and these changes or modifications should also be considered as the protection scope of the invention

The invention claimed is:

1. A liposome comprising lipid material, perfluoropropane, and prodrug,
   wherein the lipid material comprises 1,2-dipalmitoyl-sn-glycero-3-phosphocholine, DOPE-DMA, and 1,2-distearoyl-sn-glycero-3-phosphoethanolamine-polyethylene glycol,
   wherein the lipid material forms a lipid bilayer that encapsulates the perfluoropentane;
   wherein the structure of DOPE-DMA is as follows:

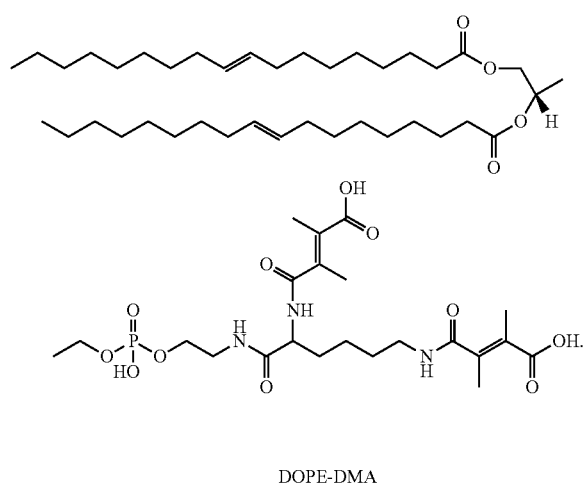

DOPE-DMA and wherein the prodrug is gemcitabine elaidate having the following structure

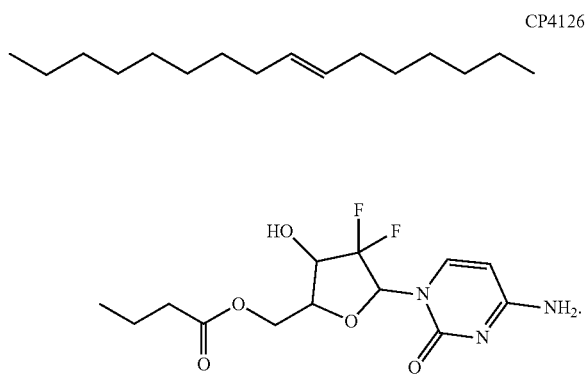

CP4126

2. The liposome of claim 1, wherein the lipid bilayer further encapsulates water, and/or a buffer solution.

3. The liposome of claim 1, wherein the 2-distearoyl-sn-glycero-3-phosphoethanolamine-polyethylene glycol is 2-distearoyl-sn-glycero-3-phosphoethanolaminepolyethylene glycol 2000.

4. The liposome of claim 1, wherein the liposome is prepared by the following method
   (i) dissolving 1.2-1.8 mg of 1,2-dipalmitoyl-sn-glycero-3-phosphocholine, 1.2-1.8 mg of DOPE-DMA, 0.8-1.2 mg of 1,2-distearoyl-sn-glycero-3-phosphoethanolaminepolyethylene glycol and 0.8-1.2 mg of gemcitabine elaidate in chloroform;
   (ii) removing the chloroform by rotary evaporation under reduced pressure to obtain the lipid film in an open round bottom flask;
   (iii) cooling the lipid film to low temperature and adding perfluoropentane to immerse the lipid film;
   (iv) adding 2.8-3.2 mL of glycerol-contained phosphate buffer saline to hydrate, stirring for 0.8-1.2 h at 2-6° C.; and
   (v) stirring for 0.8-1.2 h at 25-35° C. in the open round bottom flask to obtain the liposome.

* * * * *